US012644128B2

(12) United States Patent
Tozawa et al.

(10) Patent No.: US 12,644,128 B2
(45) Date of Patent: Jun. 2, 2026

(54) METHOD FOR PRODUCING HSL PROTEIN HAVING CATALYTIC ACTIVITY FOR 2-OXOGLUTARIC ACID-DEPENDENTLY OXIDIZING 4-HPPD INHIBITOR

(71) Applicants: National Agriculture and Food Research Organization, Tsukuba (JP); SDS Biotech K.K., Tokyo (JP)

(72) Inventors: Yuzuru Tozawa, Saitama (JP); Satomi Takei, Saitama (JP); Masahiro Oshima, Tsukuba (JP); Sakiko Hirose, Tsukuba (JP); Motoshige Kawata, Tsu (JP); Keisuke Sekino, Tokyo (JP); Akihiko Yamazaki, Tokyo (JP)

(73) Assignees: National Agriculture and Food Research Organization, Tsukuba (JP); SDS BIOTECH K.K., Tokyo (JP)

( * ) Notice: Subject to any disclaimer, the term of this patent is extended or adjusted under 35 U.S.C. 154(b) by 383 days.

(21) Appl. No.: 18/348,710

(22) Filed: Jul. 7, 2023

(65) Prior Publication Data

US 2023/0374535 A1　　Nov. 23, 2023

Related U.S. Application Data

(62) Division of application No. 16/485,046, filed as application No. PCT/JP2018/004514 on Feb. 9, 2018, now Pat. No. 11,746,357.

(30) Foreign Application Priority Data

Feb. 10, 2017　(JP) ................................. 2017-023294

(51) Int. Cl.
*C12N 15/82* (2006.01)
*C07K 14/415* (2006.01)

(52) U.S. Cl.
CPC ........ *C12N 15/8274* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 10,544,425 B2 | 1/2020 | Kato et al. | |
| 2015/0047066 A1* | 2/2015 | Kato ................... | C12Q 1/6895 536/23.6 |
| 2016/0208243 A1 | 7/2016 | Zhang et al. | |

FOREIGN PATENT DOCUMENTS

| | | |
|---|---|---|
| JP | 2014-011967 A | 1/2014 |
| WO | 2012/090950 A1 | 7/2012 |

OTHER PUBLICATIONS

Communication dated Aug. 22, 2019, issued in International Application No. PCT/JP2018/004514.
International Search Report for PCT/JP2018/004514 dated May 1, 2018 [PCT/ISA/210].

* cited by examiner

*Primary Examiner* — Mykola V. Kovalenko
(74) *Attorney, Agent, or Firm* — Sughrue Mion, PLLC

(57) ABSTRACT

A method for producing an HSL protein with increased catalytic activity to oxidize a 4-HPPD inhibitor in a 2-oxoglutarate-dependent manner is disclosed. A method for producing a plant with increased resistance to a 4-HPPD inhibitor using the method for producing the HSL protein is also disclosed. It has been revealed that, by mutating position 140 to a basic amino acid in an HSL protein, the catalytic activity of the protein to oxidize a 4-HPPD inhibitor in a 2-oxoglutarate-dependent manner can be increased, and an activity of the protein to decompose the inhibitor can be increased.

2 Claims, 16 Drawing Sheets
(1 of 16 Drawing Sheet(s) Filed in Color)

Specification includes a Sequence Listing.

ORIGINAL CULTIVAR
YAMADAWARA

HSL1
(WILD TYPE)
RECOMBINANT mHSL1
(F140H)
RECOMBINANT

FIG. 12

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| OsHSL1-mt | I | H | F | T | I | 5 |
| OsHSL1-mt | V | H | F | T | I | 5 |
| OsHSL1-mt | V | H | M | S | I | 5 |
| OsHSL1-mt | V | H | L | S | I | 4 |
| OsHSL1-mt | V | H | F | S | F | 3 |
| OsHSL1-mt | V | F | F | S | I | 3 |
| OsHSL1-mt | V | H | L | S | F | 2 |
| OsHSL1-mt | V | F | L | S | I | 1 |
| OsHSL1-mt | V | X | T | S | F | 1 |
| OsHSL1 (Wild-type) | V | F | L | S | F | ALMOST 0 |

FIG. 13

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| OsHSL2-mt | I | H | T | C | I | 2 |
| OsHSL2 (Wild-type) | I | H | T | C | F | 0 |

FIG. 14

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| ZmHSL2-mt | L | H | F | P | L | 4.5 |
| ZmHSL2-mt | L | H | Y | P | L | 4 |
| ZmHSL2 (Wild-type) | L | Q | Y | P | L | 3 |

FIG. 15

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| SbHSL1-mt | L | H | Y | P | L | 3 |
| SbHSL1 (Wild-type) | L | Q | Y | P | L | 2 |

FIG. 16

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| OsHSL1-mt | V | H | F | T | I | 5 |
| OsHSL1-mt | V | H | L | S | I | 5 |
| OsHSL1-mt | V | H | F | S | F | 5 |
| OsHSL1-mt | V | H | L | S | F | 5 |
| OsHSL1-mt | V | K | L | S | F | 4.5 |
| OsHSL1 (Wild-type) | V | F | L | S | F | 4 |
| OsHSL1-mt | V | F | F | S | F | 3.5 |
| OsHSL1-mt | V | F | L | S | I | 2.5 |
| OsHSL1-mt | V | Q | L | S | F | 2.5 |
| OsHSL1-mt | V | F | F | S | I | 1.5 |

FIG. 17

| | Position 118 | Position 140 | Position 204 | Position 229 | Position 298 | BBC-OH Decomposition Activity |
|---|---|---|---|---|---|---|
| HIS1 (Wild-type) | I | H | F | T | L | 5 |
| OsHSL1-mt | V | R | L | S | F | 5 |
| OsHSL1-mt | V | H | L | S | I | 4 |
| OsHSL1-mt | V | H | F | S | F | 4 |
| OsHSL1-mt | V | F | R | S | I | 1 |
| OsHSL1-mt | V | R | L | S | F | 0.5 |
| OsHSL1 (Wild-type) | V | F | L | S | F | ALMOST 0 |

SEQUENCE LISTING

```
Sequence total quantity: 43
SEQ ID NO: 1          moltype = DNA   length = 1056
FEATURE               Location/Qualifiers
source                1..1056
                      mol_type = other DNA
                      organism = Oryza sativa
CDS                   1..1056
SEQUENCE: 1
atggctgacg agtcatggag ggcgccggcg atagtgcaag agctggcggc agccggcgtc  60
gaggagccgc cgagccgata cctgctacgg gagaaagacc gttctgacgt caagctggtc  120
gccgccgagc tgccggagcc cctccccgtc gttgatctca gccggctaga tggtgccgag  180
gaggccacca agctcagggt ggctctgcag aattggggct tcttcctgct taccaaccat  240
ggagtagaag cctctctgat ggacagcgtg atgaacttgt cgagagagtt tttcaaccaa  300
ccaatcgaac ggaagcaaaa attcagcaac ttgatcgatg gcaagaactt ccagattcaa  360
gggtatggaa ctgaccgggt ggttacccaa gatcagatcc tggactggtc tgatcggttg  420
catctcagag ttgaacccaa ggaggagcaa gatcttgcct tctggcctga ccatcctgaa  480
tctttcaggg atgttctgaa caagtatgca tcaggaacca aaagaattag agacgatatc  540
attcaggcta tggccaagct tcttgagctt gatgaggatt acttcttgga ccgactcaac  600
gaagctcctg catttgcaag attcaactac taccctccct gtccaaggcc tgaccttgtg  660
ttcggcatca ggcctcactc cgacggcacc ctcttgacga ttcttctcgt cgacaaagat  720
gtcagtggcc tgcaagttca gagggatggc aagtggtcca acgttgaggc aactcctcac  780
acattgctga tcaacttagg tgacaccatg gaggtaatgt gcaatggcat cttcaggagc  840
ccggtgcaca gggtggtgac aaacgccgag aaggagagga tctccctggc catgttatac  900
agcgtgaacg atgagaaaga cattgagccg gcggctggtt tgctggatga gaatcggcct  960
gcaagataca ggaaagtgag cgtcgaagag ttcagggccg ggatctttgg aaaattctct  1020
cgaggagaga ggtacatcga ctccctgagg atctga                            1056
```

```
SEQ ID NO: 2               moltype = AA   length = 351
FEATURE                    Location/Qualifiers
source                     1..351
                           mol_type = protein
                           organism = Oryza sativa
SEQUENCE: 2
MADESWRAPA IVQELAAAGV EEPPSRYLLR EKDRSDVKLV AAELPEPLPV VDLSRLDGAE    60
EATKLRVALQ NWGFFLLTNH GVEASLMDSV MNLSREFFNQ PIERKQKFSN LIDGKNFQIQ   120
GYGTDRVVTQ DQILDWSDRL HLRVEPKEEQ DLAFWPDHPE SFRDVLNKYA SGTKRIRDDI   180
IQAMAKLLEL DEDYFLDRLN EAPAFARFNY YPPCPRPDLV FGIRPHSDGT LLTILLVDKD   240
VSGLQVQRDG KWSNVEATPH TLLINLGDTM EVMCNGIFRS PVHRVVTNAE KERISLAMLY   300
SVNDEKDIEP AAGLLDENRP ARYRKVSVEE FRAGIFGKFS RGERYIDSLR I            351

SEQ ID NO: 3               moltype = DNA   length = 1056
FEATURE                    Location/Qualifiers
source                     1..1056
                           mol_type = other DNA
                           organism = Oryza sativa
CDS                        1..1056
SEQUENCE: 3
atggctgacg agtcatggag gacgccggcg atagtgcaag agctggcggc ggccggcgtc    60
gaggaggccac cgagtcggta cgtgcttggg gagaaagacc gttctgacga gctggtcgcc   120
gccgagctgc cggagcccat ccccgtcgtt gatctcagcc ggctagccgg cgccgacgag   180
gctgccaagc tcaggcggc tctgcagaat tggggcttct tcctgcttac caaccatgga    240
gtagaaacct ctctgatgga tgatgtgttg aacttggcaa gagagttctt caaccaaccg    300
atcgaacgga agcgaaaatt cagcaacttg atcgacggcg agaacttcca ggtggaaggg    360
tatggaactg accgggtggt aacccaagat cagatcctgg actggtctga tcggctgttt    420
ctcagagttg aacccaagga ggagcgaaat cttgccttct ggcctgacca tcctgaatct    480
ttcagggatg ttctgaacga gtacgcatca agaaccaaaa gaataagaga cgatatcgtt    540
caggctatgt ccaagcttct tgggcttgat gaggattact tcttcgaccg actcaacaaa    600
gctcctgcac ttgcaagatt caactactac cctccctgtc caaggcctga ccttgtgttc    660
ggcgtcaggc ctcactccga cggctccctc tttacgattc ttctcgtcga cgaagatgtc    720
ggtggcctgc aaattcagag ggatggcaag tggtacaatg ttcaggtcac tcccaacaca    780
ttgctgatca acttaggtga caccatggag gtattgtgca atggcatctt caggagccca    840
gtgcacaggg tggtgacaaa cgccgagagg gagaggatc cactggccat gttttacagt    900
gtgaatgatg agaaagatat tgggccggcg gctggtttgc tggatgagaa tcggcctgca    960
agatacagga aagtgagcgt cggagagttc agggctggga tcattggaaa attctctcga   1020
cgagagagat acatcgactc cctgaagatc tgattt                            1056

SEQ ID NO: 4               moltype = AA   length = 350
FEATURE                    Location/Qualifiers
source                     1..350
                           mol_type = protein
                           organism = Oryza sativa
SEQUENCE: 4
MADESWRTPA IVQELAAAGV EEPPSRYVLG EKDRSDELVA AELPEPIPVV DLSRLAGADE    60
AAKLRAALQN WGFFLLTNHG VETSLMDDVL NLAREFFNQP IERKRKFSNL IDGKNFQVEG   120
YGTDRVVTQD QILDWSDRLF LRVEPKEERN LAFWPDHPES FRDVLNEYAS RTKRIRDDIV   180
QAMSKLLGLD EDYFFDRLNK APALARFNYY PPCPRPDLVF GVRPHSDGSL FTILLVDEDV   240
GGLQIQRDGK WYNVQTPNT LLINLGDTME VLCNGIFRSP VHRVVTNAER ERISLAMFYS   300
VNDEKDIGPA AGLLDENRPA RYRKVSVGEF RAGIIGKFSR RERYIDSLKI             350

SEQ ID NO: 5               moltype = DNA   length = 1065
FEATURE                    Location/Qualifiers
source                     1..1065
                           mol_type = other DNA
                           organism = Oryza sativa
CDS                        1..1065
SEQUENCE: 5
atggccgacg aacatggcg gttgccgaac attgtccagg aactagcagc tggagtgcaa    60
gagccaccga gtcgctacct acaagacctg gcaggcgggg atcagctggc aggagcggac   120
ataccagagc ctataccac tatagaccta ggtcgccttt ctgggtcaga cggtgctgac   180
gaagctgcca aactccgcag tgccctccag aattgggggc ctctttctgg tgtctaacca   240
tggcgtggaa acgtcgctta tgatgcggtc atcgaagcag ccaggagtt cttccggcaa   300
cctgtgtgag agaagaagaa gttgagcaac ctcatcgacg aaagcgtttt ccagattgag   360
ggctatgaca atgatcccgt ccaaaccaaa gaccagattc tcgactggag cgacaggcct   420
cacctcaaag tcgagccaga gtgcgatagg aatttggcct tttggccgac acacccgaag   480
agctttaggg acattctgca cgagtacacc ctcaagatca agacagtgaa gaacgacatc   540
ctcttggcgt tggccaagct tctcgaattg gacgaggact gcctcctgaa ccagttctcg   600
gatagggcga ttaccacagc gcgcttcaac tactactcac cctgtcccag acctgatctt   660
gtcctgggac tgaagccgca tagcgatctt tgcgctttga ccgtccttct gaccgacaaa   720
gaggtgggac gactacaagt tctccgggat ggcacttggt atctcgtaag agctgtaagg   780
gactactccc tgctgatcaa catcggccgtt acgctcgaga tcatgacgaa cgggactttt   840
cgtgccccac ttcatcgcgt ggtgaccaat cgggaacgtg agaggatgtc ggtagccatg   900
ttctatgcgt tcgatgggga gaaggagatc gagccagtgg ccgagctcct gggcctgaag   960
caacaatccg ccagatatcg cgggatcaag ggtaaggatc tcctcatcgg ccactacgag   1020
cacttctcca gaggtgggcg gggttgtgga ctcactcaaga tctga                 1065
```

-continued

```
SEQ ID NO: 6              moltype = AA  length = 354
FEATURE                  Location/Qualifiers
source                   1..354
                         mol_type = protein
                         organism = Oryza sativa
SEQUENCE: 6
MADEPWRLPN IVQELAAGVQ EPPSRYLQDL AGGDQLAGAE IPEPIPTIDL GRLSGSDGAD  60
EAAKLRSALQ NWGLFLVSNH GVETSLIDAV IEAAREFFRQ PVEEKKKLSN LIDGKRFQIE  120
GYGNDPVQTK DQILDWSDRL HLKVEPECDR NLAFWPTHPK SFRDILHEYT LKIKTVKNDI  180
LLALAKLLEL DEDCLLNQFS DRAITTARFN YYSPCPRPDL VLGLKPHSDL CALTVLLTDK  240
EVGGLQVLRD GTWYSVPAVR DYSLLINIGV TLEIMTNGTF RAPLHRVVTN AERERMSVAM  300
FYAVDGEKEI EPVAELLGLK QQSARYRGIK GKDLLIGHYE HFSRGGRVVD SLKI        354

SEQ ID NO: 7              moltype = DNA  length = 1059
FEATURE                  Location/Qualifiers
source                   1..1059
                         mol_type = other DNA
                         organism = Hordeum vulgare
CDS                      1..1059
SEQUENCE: 7
atggcggcgt ccgatgaaat gccgatggtt caagacctag tttcggctgg cgttcaagag  60
cctcccagtc ggtacctcgt gcacgagcaa gatcgccatg gcgacctcct tgccgcacat  120
gagatgcccg agccaattcc gctgattgac ctatctcgcc ttatggacgc cgatgaggca  180
gacaagctca gagctgcgtt gcaaacttgg ggcttctttc tcgcgacaaa ccacggcata  240
gaggactcct tgatggaggc catgatgtct gcgtcgaagg agttcttccg tcagccaagc  300
gaagagaagc agaaatgctc caatctggtg gatgggaatg gcaagcacta tcaggtcgaa  360
ggttacggat cagacaaggt cgagtcagag gaccaagtcc tcaactggaa cgataggctg  420
cacttgaggg tagaaccgga ggacgaacgc aatttcgcca aatggccttc tcacccagag  480
tcattccgtg acgtgctcaa cgagtacgcg agcaagacga agagatcag ggacttggtg  540
ctacgcagca tcgccaaact cctggagatt gatgaggact acttcgtgaa tcagatctcc  600
aacaaagcat ccggttttgc caggctctac tactatccgc cctgtcctag gcccgacctt  660
gtactcggac tcactccgca ttcggacggg aatttgctca ccatcctgtt cgttgacgat  720
gacgtcggtg gccttcaggt ccaacgggat gggaagtggt acaacgtgcc agcaaagcca  780
catacgctgg tgatcaacct tgccgattgc ctggagatca tgaacaacgg gatattccgg  840
agtcccgttc acagggtcgt cacaaacacc gagaaggagc ggctgagcct cgctgtgttc  900
tatgccgttg atgaagaaac cgtgttggaa ccagctcctg gactccttga cgagaagagg  960
ccaccaagat accgcaagat gatggccaag gactttgtcg tgggactgtt cgagcacttt  1020
ctgcagggca gcgctttat cgataccctc aagatgtga                        1059

SEQ ID NO: 8              moltype = AA  length = 352
FEATURE                  Location/Qualifiers
source                   1..352
                         mol_type = protein
                         organism = Hordeum vulgare
SEQUENCE: 8
MAASDEMPMV QDLVSAGVQE PPSRYLVHEQ DRHGDLLAAH EMPEPIPLID LSRLMDADEA  60
DKLRAALQTW GFFLATNHGI EDSLMEAMMS ASREFFRQPS EEKQKCSNLV DGNGKHYQVE  120
GYGSDKVESE DQVLNWNDRL HLRVEPEDER NFAKWPSHPE SFRDVLNEYA SKTKKIRDLV  180
LRSIAKLLEI DEDYFVNQIS NKASGFARLY YPPCPRPDL VLGLTPHSDG NLLTILFVDD  240
DVGGLQVQRD GKWYNVPAKP HTLVINLADC LEIMNNGIFR SPVHRVVTNT EKERLSLAVF  300
YAVDEETVLE PAPGLLDEKR PPRYKMMAK DFVVGLFEHF LQGKRFIDTL KM          352

SEQ ID NO: 9              moltype = DNA  length = 1068
FEATURE                  Location/Qualifiers
source                   1..1068
                         mol_type = other DNA
                         organism = Hordeum vulgare
CDS                      1..1068
SEQUENCE: 9
atggcggatg cagaaccctg gaaaacagtg aagataccgc cgatagtgca ggaactggca  60
acaggtgtgc aagagccacc atcccggtat gtaatcgccg agcataaccg cccagctgtg  120
gctgcctccg aaatgccgga ccctattccc atcgttgacc tttctcgctt gtccgacaac  180
tgtgccgatg aagttgccaa gttgcgctca gcgctcgaaa actggggctt gttcctccgca  240
gtcgggcacg gaatggagca aagctttctc ggtgaggtca tgaaggttgc gagggagttc  300
tttaagctac ctttggagga gaagcagaag tactcgaacc ttgtgaacgg cgacgaggtt  360
cgcattgaag gctatgggaa tgacatggtc gtgagcgaga agcaaatcct cgattggtgc  420
gatagactgt acatcatcgt tgagccagag aacagacgga tctacagtct ctggccgact  480
caaccacctt ccttccgtga catcctcagc gagtacaccg tgagtgcca taagatcgct  540
aacctgttcc tccagaatct ggcgaagcta ctcgacctcc atgaggacta cttcgtcaac  600
atgttcgacg agaacgctct tgcgtatgcc aggctcaact actacccgaa ttgcccgaaa  660
cccgatcacg tgtttggcat gaaacctcac acggacgcgt cggtcattac catcgtgttc  720
attgacgaca atgtcagtgg cctacaactc cagaacgatg gagtctggta caatgtgccc  780
attgtaccca atgtccttcc cgttcaacgtt ggggatgtaa tggagatcat gcaaacggc  840
ttcttcaagt ctccaatcca cagggttgtg acgaatgcag agaaagagag gctgagcttg  900
gtgatgttct acaccatgaa ccccgaaaag gagatagagc cactgccaga gcttgtcgat  960
gaaaagaggc cacggaggta tcgcaagacg actaccaacg actacatcgc taagctgttt  1020
gagacatttg cccgtggaac tctggccatt gacaccgtca agatctga               1068
```

-continued

```
SEQ ID NO: 10            moltype = AA   length = 355
FEATURE                  Location/Qualifiers
source                   1..355
                         mol_type = protein
                         organism = Hordeum vulgare
SEQUENCE: 10
MADAEPWKTV KIPPIVQELA TGVQEPPSRY VIAEHNRPAV AASEMPDPIP IVDLSRLSDN   60
CADEVAKLRS ALENWGLFLA VGHGMEQSFL GEVMKVAREF FKLPLEEKQK YSNLVNGDEV  120
RIEGYGNDMV VSEKQILDWC DRLYIIVEPE NRRIYSLWPT QPPSFRDILS EYTVRCHKIA  180
NLFLQNLAKL LDLHEDYFVN MFDENALAYA RLNYYPNCPK PDHVFGMKPH TDASVITIVF  240
IDDNVSGLQL QNDGVWYNVP IVPNALLVNV GDVMEIMSNG FFKSPIHRVV TNAEKERLSL  300
VMFYTMNPEK EIEPLPELVD EKRPRRYRKT TTNDYIAKLF ETFARGTLAI DTVKI       355

SEQ ID NO: 11            moltype = DNA   length = 1071
FEATURE                  Location/Qualifiers
source                   1..1071
                         mol_type = other DNA
                         organism = Hordeum vulgare
CDS                      1..1071
SEQUENCE: 11
atggctagct atgatcagca gttcaagatt ctcgaggtcc ctccaattgt ccaagagctc   60
gttggtgcgg gtgtgaagga gccaccatct caatacgtct tgccggagca atatcgccct  120
gcagctgccg cagtgtcgga gatgccagaa cccataccga tcatcgacct atcgaggctg  180
tcagccggat ctgctgaaga gttcgacaaa ctccgtagtg ccctagagaa ctggaatctc  240
tttctggccg ttggccatgg catggaaccc tccttcttgg cggaagccat gaaggcaacg  300
cgcgagttct ttaacctctc aatcgaggag aagcagaaca agtcggaggc  360
gagaaaatgg ggatggatgg ctatggcaac gatatggtgg tcaaggaaaa ccaggtgctg  420
gattggaacg acagactcaa cctcctcgtt gagccagagt cattgcgtac ctacaggctc  480
tggcctactc aaccgccgtc gtttagggac gttctctgcg aatacaccgt gcggtgtaag  540
gcggcgacca acatcgtgat acgcaacatg gccaagatgc tgaatcttca gaggagcac  600
cttgtgaaca tgatcggaga caactccatc acacaggcca tcttcaacta ctatccccaa  660
tgcccaagac ccgaccatgt cctcggtctg aaagcccaca cagatggatc catcatcacc  720
gtaaacttcg ccgatgccga agggcttcaa ctagagcgga atggcgtgtg gtacaatgtc  780
ccgattgtcc ccaatgcgct tgtcatgaac attggggaca tcatggagat cctgagcaat  840
ggcttctta agagcctggt acacaggggt gttacgaacg ctgagaagga acggctcagt  900
cttgtcctgg tgtacacact cgaactcgag actcaactgg agcctgtgag cgagttggtt  960
gacgacaaac gcccagctag gtacatgaag attaagctga atgactacat ggagaagtac 1020
cacgatacgt acgcaaccgg cactttggcg attgacgggg tgaagatctg a          1071

SEQ ID NO: 12            moltype = AA   length = 356
FEATURE                  Location/Qualifiers
source                   1..356
                         mol_type = protein
                         organism = Hordeum vulgare
SEQUENCE: 12
MASYDQQFKI LEVPPIVQEL VGAGVKEPPS QYVLPEQYRP AAAAVSEMPE PIPIIDLSRL   60
SAGSAEEFDK LRSALENWNL FLAVGHGMEP SFLAEAMKAT REFFNLSIEE KQKYSNIVGG  120
EKMGMDGYGN DMVVKENQVL DWNDRLNLLV EPESLRTYRL WPTQPPSFRD VLCEYTVRCK  180
AATNIVIRNM AKMLNLQEEH LVNMIGDNSI TQAIFNYYPQ CPRPDHVLGL KAHTDGSIIT  240
VNFADAEGLQ LERNGVWYNV PIVPNALVMN IGDIMEILSN GFFKSLVHRV VTNAEKERLS  300
LVLVYTLELE TQLEPVSELV DDKRPARYMK IKLNDYMEKY HDTYATGTLA IDGVKI      356

SEQ ID NO: 13            moltype = DNA   length = 1071
FEATURE                  Location/Qualifiers
source                   1..1071
                         mol_type = other DNA
                         organism = Triticum aestivum
CDS                      1..1071
SEQUENCE: 13
atggccgctt ctgacgaatc accgatggtt cggccaactg tccaagagct taccgcggca   60
ggagtggagg aaccaccgag gcagtacgtg ctccccgagc aagatcgcca tggcgaccta  120
cttgccgccg acgagtttcc ggaacccaca ccgctgatcg acctaagccg tctaaccgat  180
gcggatgagg ccgaaagact ccgtgctgcg ttgcagactt ggggcttctt cctcgctacg  240
aatcatggca ttgaggactc acttatggac gccatgatgt ccgtttccag agagttcttc  300
aggcaaccag ccgaggagaa gcagaagtgc agcaacctgg tcgatgggaa tggtaaggac  360
taccaggtag agggatatgg cagtgacaag gtggtgtccg aagatcaagt cctcaactgg  420
agtgacaggc tgcacttgag agtcgaacca gaggacgaga gaaacttcgc caaatgccac  480
tctcacccag agtcgtttcg tgacgtgctg caagagtatg cctctcgcac caagaagatc  540
agggatcttg ccttcgctc aattgctgag ctgctcgaga ttgacgagga ttacttcgtc  600
aaccaaattt cgaacaaggc atccggcttt gcgcgcttca actactaccc tccttgtcca  660
cgccccgatt tggtgcttgg gttgaggcct cactcggacg gaggtctgct cacgatcctg  720
ttcaatgacg acaagattgg tgactccaga atacagaggg atgggaggtg gtacaatgtg  780
ccgacgaaac cccacactct gctcatcaac ctcgcagact gcctggaaat catgaacaat  840
ggcatcttta ggtccccgtt ccatcgggtt gtgaccaacg tggagaagga ccgcttgagc  900
ctcgcggttt ctacgccgt agatgcggag acaatgctcg aacccgctcc aggcctcctg  960
gatgacaaga ggcctagccg gtatcggaag atgttggcca aggactttgt cgcaggcctc 1020
ttcgagcact tccgccaagg gaaacggttt atcgacaccc tcaagatatg a          1071
```

```
SEQ ID NO: 14             moltype = AA   length = 356
FEATURE                   Location/Qualifiers
source                    1..356
                          mol_type = protein
                          organism = Triticum aestivum
SEQUENCE: 14
MAASDESPMV RPTVQELTAA GVEEPPRQYV LPEQDRHGDL LAADEFPEPT PLIDLSRLTD  60
ADEAERLRAA LQTWGFFLAT NHGIEDSLMD AMMSVSREFF RQPAEEKQKC SNLVDGNGKD  120
YQVEGYGSDK VVSEDQVLNW SDRLHLRVEP EDERNFAKWP SHPESFRDVL QEYASRTKKI  180
RDLVLRSIAE LLEIDEDYFV NQISNKASGF ARFNYYPPCP RPDLVLGLRP HSDGGLLTIL  240
FNDDNVGGLQ IQRDGRWYNV PTKPHTLLIN LADCLEIMNN GIFRSPFHRV VTNVEKDRLS  300
LAVFYAVDAE TMLEPAPGLL DDKRPSRYRK MLAKDFVAGL FEHFRQGKRF IDTLKI       356

SEQ ID NO: 15             moltype = DNA   length = 1020
FEATURE                   Location/Qualifiers
source                    1..1020
                          mol_type = other DNA
                          organism = Triticum aestivum
CDS                       1..1020
SEQUENCE: 15
atgcaagagc ctccgtcaca gtacttgttg cgcgagcaag agctgcttgg agctcatctc  60
gctggggctg agatgcccga accagtgccg acgattgacc taggtctgtt gtcggcttcg  120
aacgatccgg aagaagccgc aaaactgcgt tctgcccttc agacctgggg tttcttccaa  180
gtcagcaacc atggcatgga ggcctcaatg atggactccg tctttaccgc gtctagggaa  240
ttcttccatc tccctctcga agagaagaag aagtgcagta acctgatcga tggaaagcac  300
ttccaggttg agggctatgg caacgaccaa gtacgcactc aggaccagag gctagattgg  360
agcgatcggc ttcacctccg tgtcgagcca gaaggaggac gcaatctcgt gcactggcct  420
acccacccca agtcctttcg cgatgacctc acgagtaca ccctcaagtg caagcgcatt  480
aagggcgaca tactgagggc aatggccaag atccttagc tcgacgagga ttgcctcgtg  540
aaccagttca acagcaatgc acccacattt gcacggttca accactttcc accgtgcccc  600
agaccagatc tcgtgctggg catcaaaccg catgccgact ttcccgcctt gactgtcctg  660
ttgatggaca aggatgtcgc tggccttcag tacctcaaag acgggacatg gtacaacgtt  720
ccggcggcct gtgaccacac tctactgatc agcattggcc tcaccatgga gatcatgacg  780
aatgggatgt tcacagggcc aatgcacagg gttgtcacga atgcggacaa ggagaggatt  840
tccgtggcga tgttctatgg ggtggaccct gagcaagaga tcggtccaat agcccacctc  900
ttgtccgaag agcaaccagc gcaataccgg aagatgaaag ccaacgacct tctggttctc  960
catcacgagc attacgccgg tggcagaggc ccaaggatcg cggatgcgct gaagatctga  1020

SEQ ID NO: 16             moltype = AA   length = 339
FEATURE                   Location/Qualifiers
source                    1..339
                          mol_type = protein
                          organism = Triticum aestivum
SEQUENCE: 16
MQEPPSQYLL REQELLGAHL AGAEMPEPVP TIDLGLLSAS NDPEEAAKLR SALQTWGFFQ  60
VSNHGMEASM MDSVFTASRE FFHLPLEEKK KCSNLIDGKH FQVEGYGNDQ VRTQDQRLDW  120
SDRLHLRVEP EGGRNLVHWP THPKSFRDDL HEYTLKCKRI KGDILRAMAK ILELDEDCLV  180
NQFNSNAPTF ARFNHFPPCP RPDLVLGIKP HADFPALTVL LMDKDVAGLQ YLKDGTWYNV  240
PAACDHTLLI SIGLTMEIMT NGMFTGPMHR VVTNADKERI SVAMFYGVDP EQEIGPIAHL  300
LSEEQPAQYR KMKANDLLVL HHEHYAGGRG PRIADALKI                         339

SEQ ID NO: 17             moltype = DNA   length = 1065
FEATURE                   Location/Qualifiers
source                    1..1065
                          mol_type = other DNA
                          organism = Zea mays
CDS                       1..1065
SEQUENCE: 17
atggctgatg aatcgtggcg cgtcccaact cccgtccaag aactcgccgc gggtgtagtt  60
gagccaccta cacagttcgt tctccaagag caagatagac caggctcagg acgctcctc  120
tttgccaccg atatgccgga gccaattccg gtcgtggacc ttttccaggct cgctgctgcc  180
gatgaagcga gcaaactgcg gtcagctctg gagacttggg gcctttttcct cgtcacaaag  240
cacggcatcg aggcgtcctt gatggatgac gtgatggcag catctcgcga cttcttctac  300
caacctctgg aggccaagca agagtacagc aacctcattg gaggcaagag gtttcagatg  360
gagggctatg ggaacgacat ggtcaagtcg aaagaccaga tcctcgactg gcaggatagg  420
ctgcagctgc gtgttgagcc gcaagacgag cggaacttgg cctactgacg caaacatccg  480
gactcgttta gggacctact cgaaaagtac gccagcaaaa ccaagatagt ccggaacaag  540
gtgcttcgcg ctatgggtaa gactctcgag cttggcgagg actacttcat ctcccagatt  600
ggcgatcgtc gtcagccat agcacgcttc aactactatc accgtgccc aagacccgat  660
cttgtgttcg ggatcaagcc tcacagtgac ggaggcgcgg tcaccatact gctggttgac  720
aaggatgtgg gtgcttgca agtgcagaag gacggagtgt ggtacacggt cccatccatg  780
ccgcataccc tgctagtgaa tctcggcgac agcatggaga tcatgaataa cggtatcttc  840
aagtctcccg tacacagagt ggtgaccaat gcggagaagg aacggctgag tctagccatg  900
ttttacgggg ttgagggaca acgcgttctg gagccagcgc tcggcttgct cggtgaggaa  960
cgtcctgcaa ggtatcgcaa gatcatggcc tccgactaca tcatcgggtt gaggcaaggg  1020
attgccgagg gacagaggtt catcgaaacg ctcaagattt gataa                  1065
```

-continued

```
SEQ ID NO: 18          moltype = AA  length = 353
FEATURE                Location/Qualifiers
source                 1..353
                       mol_type = protein
                       organism = Zea mays
SEQUENCE: 18
MADESWRVPT PVQELAAGVV EPPTQFVLQE QDRPGSGTLL FATDMPEPIP VVDLSRLAAA  60
DEASKLRSAL ETWGLFLVTK HGIEASLMDD VMAASRDFFY QPLEAKQEYS NLIGGKRFQM  120
EGYGNDMVKS KDQILDWQDR LQLRVEPQDE RNLAYWPKHP DSFRDLLEKY ASKTKIVRNK  180
VLRAMGKTLE LGEDYFISQI GDRASAIARF NYYPPCPRPD LVFGIKPHSD GGAVTILLVD  240
KDVGGLQVQK DGVWYTVPSM PHTLLVNLGD SMEIMNNGIF KSPVHRVVTN AEKERLSLAM  300
FYGVEGQRVL EPALGLLGEE RPARYRKIMA SDYIIGLRQG IAEGQRFIET LKI          353

SEQ ID NO: 19          moltype = DNA  length = 1059
FEATURE                Location/Qualifiers
source                 1..1059
                       mol_type = other DNA
                       organism = Zea mays
CDS                    1..1059
SEQUENCE: 19
atggcggtcg agagctggac agtgcctacg ccggtcaagg accttgctgc cctcgttgat  60
gagcctccct ccaggttcgt ccagagggaa gagcataggc ctggttcct gatgcttgcc   120
gcagacatgc cggatccgct gccaattgtg gacctcaaca agcttagcac tgcagacgaa   180
gccgcgaaac tgcgttcagc gctgcaaaca tggggtcttt cctcgccac caatcacgga   240
atcgacgcta gcctcatgga ggacctcatg gaagcctcac gggagttctt ccaccaaccg   300
ctacaggaac gccagaagta ctcgaacttg cgcgaaggca ctcggtttca gctcgagggc   360
tacgggagtg accccgtagt ggcccaggac cacatcttgg actggaatga caggttgcag   420
ctaaaggtcg agcagagga tgagagatcg ctggcacaat ggccgaagta ccctgagtcc    480
tttcgcgatc tcctacacga gtatgcgtcc aagacgaagt ctatgaggga tcggattttg   540
cgtgctatgg cgaagatcct cgagcttgac gaggaggaat tcatcaagca gctgggagca   600
agtccccaag cctatgcccg cttcaactac tacccaccat gcccaaggcc agagctcgtt   660
ctgggcatca aagcgcactc agacggccca gtgctcaccg ttctgctggt agatagggag   720
gtcggtgggt tgcaagtgca aagagagaac acctggttta acgttccctt tgtgccacat   780
accctcgtga tcaacctggg cgatagccta gagatcatgt ccaatgggat cttcaagtct   840
cccgtccata gggtcgtgac gaatgccgag aaagagcgca tttctctggc tatgctctac   900
gcggttgaac gggataacgt gttgcaacca gccgctgggc tcctcgacga gaaacgtccg   960
gcacgctata gacgcataac tgaggccgac ttccttgagg gagtcaagga cacttctcg   1020
aagggcattc ggatgatcga aaccctcaag atatgataa                         1059

SEQ ID NO: 20          moltype = AA  length = 351
FEATURE                Location/Qualifiers
source                 1..351
                       mol_type = protein
                       organism = Zea mays
SEQUENCE: 20
MAVESWTVPT PVKDLAALVD EPPSRFVQRE EHRPGSLMLA ADMPDPLPIV DLNKLSTADE  60
AAKLRSALQT WGLFLATNHG IDASLMEDLM EASREFFHQP LQERQKYSNL REGTRFQLEG  120
YGSDPVVAQD HILDWNDRLQ LKVEPEDERS LAQWPKYPES FRDLLHEYAS KTKSMRDRIL  180
RAMAKILELD EEEFIKQLGA SPQAYARFNY YPPCPRPELV LGIKAHSDGP VLTVLLVDRE  240
VGGLQVQREN TWFNVPFVPH TLVINLGDSL EIMSNGIFKS PVHRVVTNAE KERISLAMLY  300
AVERDNVLQP AAGLLDEKRP ARYRRITEAD FLEGVKEHFS KGIRMIETLK I           351

SEQ ID NO: 21          moltype = DNA  length = 1059
FEATURE                Location/Qualifiers
source                 1..1059
                       mol_type = other DNA
                       organism = Sorghum bicolor
CDS                    1..1059
SEQUENCE: 21
atggcagggg aatcgtggaa ggttccgaca cccgtcaaag acttggcagc gctcgtagaa  60
gagccaccat cccagttcgt acagagggag gaggaccgtc ccggctcgct catgctggca   120
gcggatatgc cagatccact ccccatagtg gaccttgaca agatgagcac agctgatgag   180
gctaccaaac tacgctctgc cctccaaact tggggacttt ccttgccac caatcacgga    240
atcgatgtca gcttgatgga ggacctgatg aaggccagta gggagttct caaccagcca    300
ctgcaagaga ggcaaaagta ctccaatctc agagaaggca cgcggtttca gctcgagggg   360
tatgcagcg atccggtgat agcccaagac cacattctcg actggagcga cagactccaa    420
ctgaaggttg agcggagga tgaacggaat ctcgctcaat ggccaaaaca ccccgaatcc    480
tttcgcgacc tcctgcatga gtacgcgacc aagacaaaga ctgtcatggt gaagatcctc    540
cgggcaatgg ctaagaccct agagttggac gaggaggact tcatcgacca gattggcggt   600
aggccccaag cttatgcccg tttcaactac taccgccat gccctagacc cgaactggtg    660
ttggggatca aagcgcattc cgacggtcca cttctgaccg tcttgctggt cgatcgcgaa    720
gtcggcggac tacagattca gcgcgaaaac aagtggttca acgtgccatc aatacctcat   780
gcccgttcaa cgagactctc tgagatcatg caaacgggat ctttaagagt                840
ccggttcaca gggttgtgac gaatgcgag aaagagcgca tttcgcttgc catgctctac    900
gccgttcaac gcgataacgt gcttgagcct gcgcctggct tgctggatga gaagcggccg   960
gccaagtaca ggcgtatcac ggaagcccac tttctggagg gagtgaagga gcacttctca    1020
aagggtatga ggatgatcga gactctgaag atctgataa                          1059
```

-continued

```
SEQ ID NO: 22            moltype = AA   length = 351
FEATURE                  Location/Qualifiers
source                   1..351
                         mol_type = protein
                         organism = Sorghum bicolor
SEQUENCE: 22
MAGESWKVPT PVKDLAALVE EPPSQFVQRE EDRPGSLMLA ADMPDPLPIV DLDKMSTADE   60
ATKLRSALQT WGLFLATNHG IDVSLMEDLM KASREFFNQP LQERQKYSNL REGTRFQLEG  120
YGSDPVIAQD HILDWSDRLQ LKVEPEDERN LAQWPKHPES FRDLLHEYAT KTKTVMVKIL  180
RAMAKTLELD EEDFIDQIGG RPQAYARFNY YPPCPRPELV LGIKAHSDGP LLTVLLVDRE  240
VGGLQIQREN KWFNVPSIPH ALVINLGDSL EIMSNGIFKS PVHRVVTNAE KERISLAMLY  300
AVQRDNVLEP APGLLDEKRP AKYRRITEAH FLEGVKEHFS KGMRMIETLK I           351

SEQ ID NO: 23            moltype =   length =
SEQUENCE: 23
000

SEQ ID NO: 24            moltype = DNA   length = 40
FEATURE                  Location/Qualifiers
misc_feature             1..40
                         note = Artificially synthesized primer sequence
source                   1..40
                         mol_type = other DNA
                         organism = synthetic construct
SEQUENCE: 24
cgacggcaag aacttccaga ttgaagggta tggaactgac                          40

SEQ ID NO: 25            moltype = DNA   length = 40
FEATURE                  Location/Qualifiers
misc_feature             1..40
                         note = Artificially synthesized primer sequence
source                   1..40
                         mol_type = other DNA
                         organism = synthetic construct
SEQUENCE: 25
gtcagttcca tacccttcaa tctggaagtt cttgccgtcg                          40

SEQ ID NO: 26            moltype = DNA   length = 32
FEATURE                  Location/Qualifiers
misc_feature             1..32
                         note = Artificially synthesized primer sequence
source                   1..32
                         mol_type = other DNA
                         organism = synthetic construct
SEQUENCE: 26
ggtctgatcg gctgcatctc agagttgaac cc                                  32

SEQ ID NO: 27            moltype = DNA   length = 32
FEATURE                  Location/Qualifiers
misc_feature             1..32
                         note = Artificially synthesized primer sequence
source                   1..32
                         mol_type = other DNA
                         organism = synthetic construct
SEQUENCE: 27
gggttcaact ctgagatgca gccgatcaga cc                                  32

SEQ ID NO: 28            moltype = DNA   length = 39
FEATURE                  Location/Qualifiers
misc_feature             1..39
                         note = Artificially synthesized primer sequence
source                   1..39
                         mol_type = other DNA
                         organism = synthetic construct
SEQUENCE: 28
caacaaagct cctgcatttg caagattcaa ctactaccc                           39

SEQ ID NO: 29            moltype = DNA   length = 39
FEATURE                  Location/Qualifiers
misc_feature             1..39
                         note = Artificially synthesized primer sequence
source                   1..39
                         mol_type = other DNA
                         organism = synthetic construct
SEQUENCE: 29
gggtagtagt tgaatcttgc aaatgcagga gctttgttg                           39

SEQ ID NO: 30            moltype = DNA   length = 34
FEATURE                  Location/Qualifiers
```

```
misc_feature            1..34
                        note = Artificially synthesized primer sequence
source                  1..34
                        mol_type = other DNA
                        organism = synthetic construct
SEQUENCE: 30
cctcactccg acggcaccct ctttacgatt cttc                                    34

SEQ ID NO: 31           moltype = DNA  length = 34
FEATURE                 Location/Qualifiers
misc_feature            1..34
                        note = Artificially synthesized primer sequence
source                  1..34
                        mol_type = other DNA
                        organism = synthetic construct
SEQUENCE: 31
gaagaatcgt aaagagggtg ccgtcggagt gagg                                    34

SEQ ID NO: 32           moltype = DNA  length = 38
FEATURE                 Location/Qualifiers
misc_feature            1..38
                        note = Artificially synthesized primer sequence
source                  1..38
                        mol_type = other DNA
                        organism = synthetic construct
SEQUENCE: 32
ggatctcact ggccatgtta tacagtgtga atgatgag                                38

SEQ ID NO: 33           moltype = DNA  length = 38
FEATURE                 Location/Qualifiers
misc_feature            1..38
                        note = Artificially synthesized primer sequence
source                  1..38
                        mol_type = other DNA
                        organism = synthetic construct
SEQUENCE: 33
ctcatcattc acactgtata acatggccag tgagatcc                                38

SEQ ID NO: 34           moltype = DNA  length = 24
FEATURE                 Location/Qualifiers
misc_feature            1..24
                        note = Artificially synthesized primer sequence
source                  1..24
                        mol_type = other DNA
                        organism = synthetic construct
SEQUENCE: 34
ttgtatgcgg tcgatgggga gaag                                               24

SEQ ID NO: 35           moltype = DNA  length = 23
FEATURE                 Location/Qualifiers
misc_feature            1..23
                        note = Artificially synthesized primer sequence
source                  1..23
                        mol_type = other DNA
                        organism = synthetic construct
SEQUENCE: 35
catggctacc gacatcctct cac                                                23

SEQ ID NO: 36           moltype = DNA  length = 22
FEATURE                 Location/Qualifiers
misc_feature            1..22
                        note = Artificially synthesized primer sequence
source                  1..22
                        mol_type = other DNA
                        organism = synthetic construct
SEQUENCE: 36
catctaaagg tcgagccaga gg                                                 22

SEQ ID NO: 37           moltype = DNA  length = 25
FEATURE                 Location/Qualifiers
misc_feature            1..25
                        note = Artificially synthesized primer sequence
source                  1..25
                        mol_type = other DNA
                        organism = synthetic construct
SEQUENCE: 37
caacctgtca ttccagtcca agatg                                              25
```

-continued

```
SEQ ID NO: 38          moltype = DNA  length = 22
FEATURE                Location/Qualifiers
misc_feature           1..22
                       note = Artificially synthesized primer sequence
source                 1..22
                       mol_type = other DNA
                       organism = synthetic construct
SEQUENCE: 38
catctgaagg ttgagccgga gg                                           22

SEQ ID NO: 39          moltype = DNA  length = 25
FEATURE                Location/Qualifiers
misc_feature           1..25
                       note = Artificially synthesized primer sequence
source                 1..25
                       mol_type = other DNA
                       organism = synthetic construct
SEQUENCE: 39
gagtctgtcg ctccagtcga gaatg                                        25

SEQ ID NO: 40          moltype = DNA  length = 21
FEATURE                Location/Qualifiers
misc_feature           1..21
                       note = Artificially synthesized primer sequence
source                 1..21
                       mol_type = other DNA
                       organism = synthetic construct
SEQUENCE: 40
tttgcccgct tcaactacta c                                            21

SEQ ID NO: 41          moltype = DNA  length = 17
FEATURE                Location/Qualifiers
misc_feature           1..17
                       note = Artificially synthesized primer sequence
source                 1..17
                       mol_type = other DNA
                       organism = synthetic construct
SEQUENCE: 41
ggcttgggga cttgctc                                                 17

SEQ ID NO: 42          moltype = DNA  length = 28
FEATURE                Location/Qualifiers
misc_feature           1..28
                       note = Artificially synthesized primer sequence
source                 1..28
                       mol_type = other DNA
                       organism = synthetic construct
SEQUENCE: 42
cgcatcaggc aggaaatatt taggtgac                                     28

SEQ ID NO: 43          moltype = DNA  length = 28
FEATURE                Location/Qualifiers
misc_feature           1..28
                       note = Artificially synthesized primer sequence
source                 1..28
                       mol_type = other DNA
                       organism = synthetic construct
SEQUENCE: 43
ggagaaaggc ggacaggtat ccggtaag                                     28
```

METHOD FOR PRODUCING HSL PROTEIN HAVING CATALYTIC ACTIVITY FOR 2-OXOGLUTARIC ACID-DEPENDENTLY OXIDIZING 4-HPPD INHIBITOR

CROSS REFERENCE TO RELATED APPLICATIONS

This application is a Divisional of U.S. application Ser. No. 16/485,046, filed Aug. 9, 2019, which is a National Stage of International Application No. PCT/JP2018/004514 filed Feb. 9, 2018, claiming priority based on Japanese Patent Application No. 2017-023294 filed Feb. 10, 2017, the contents of all of which are incorporated herein by reference in their entirety.

INCORPORATION BY REFERENCE OF SEQUENCE LISTING

The content of the electronically submitted sequence listing, filename: SEQ_LIS_ST26_AS_FILED.xml; size: 63,084 bytes; and date of creation: Jun. 28, 2023, filed herewith, is incorporated herein by reference in its entirety.

DESCRIPTION

Technical Field

The present invention relates to a method for producing an HSL protein with increased catalytic activity to oxidize a 4-HPPD inhibitor in a 2-oxoglutarate-dependent manner. In addition, the present invention relates to a method for producing a plant with increased resistance to a 4-HPPD inhibitor, utilizing the above method. Moreover, the present invention also relates to a method for determining resistance of a plant to a 4-HPPD inhibitor and a method for breeding a plant having increased resistance to a 4-HPPD inhibitor, utilizing the above method.

Background Art

These days, herbicide components such as benzobicyclon, tefuryltrione, sulcotrione, mesotrione, and tembotrione have been developed and put into practice. These herbicides are all agents (4-HPPD inhibitors) that inhibit the function of 4-hydroxyphenylpyruvate dioxygenase (4-HPPD), and by inhibiting the function of this enzyme, indirectly inhibit the carotenoid synthesis system to cause chlorophyll degradation, whitening plants and withering the plants to death, as shown in FIG. 1. Since the safety to edible cultivars was sufficiently confirmed, these inhibitors have been spreading rapidly in cultivation of rice, and the like.

Meanwhile, some cultivars are weak to the 4-HPPD inhibitors, and it has been reported that there is a possibility that some cultivars are withered to death in some cases. For this reason, there have been demands for the developments of a method for increasing resistance to 4-HPPD inhibitors and a method for reliably identifying resistance or susceptibility to the 4-HPPD inhibitors.

Regarding this point, the present inventors previously found out that a gene (4-hydroxyphenylpyruvate dioxygenase inhibitor sensitive gene No. 1 (HIS1)), which rice has and codes for an oxidase (2-oxoglutarate-dependent dioxygenase) dependent on the divalent iron ion and 2-oxoglutarate, and a homologous gene thereof (HSL1 gene) contribute to the resistance or the susceptibility to the 4-HPPD inhibitors. The present inventors also found that a plant with increased resistance or susceptibility to a 4-HPPD inhibitor can be produced utilizing the gene, and further found that genes having a high homology with the HIS1 gene of rice also existed in barley, sorghum, corn, and the like (PTL 1).

CITATION LIST

Patent Literature

[PTL 1] International Publication No. WO2012/090950

SUMMARY OF INVENTION

Technical Problem

An object of the present invention is to provide a method for producing an HSL protein with increased catalytic activity to oxidize a 4-HPPD inhibitor in a 2-oxoglutarate-dependent manner. Moreover, another object of the present invention is to provide a method for producing a plant with increased resistance to a 4-HPPD inhibitor, utilizing the above method. In addition, still another object of the present invention is to provide a method for determining resistance of a plant to a 4-HPPD inhibitor, and a method for breeding a plant having increased resistance to a 4-HPPD inhibitor, utilizing the above method.

Solution to Problem

As a result of repeated earnest studies, the present inventors have confirmed that the HIS1 protein of rice has an activity to oxidize a 4-HPPD inhibitor in a 2-oxoglutarate-dependent manner and thus decompose the inhibitor. However, on the other hand, the present inventors also found that an OsHSL1 protein exhibiting a high homology with the HIS1 protein (a protein having an amino acid sequence of SEQ ID NO: 4) has little catalytic activity.

Based on the new findings, the present inventors surmised that a slight difference in amino acid sequence between the HIS1 protein and the OsHSL1 protein contributed to the catalytic activity. Then, the present inventors prepared mutants by substituting amino acid residues at sites which were surmised to contribute to these catalytic activities in the OsHSL1 proteins with corresponding amino acid residues of the HIS1 protein and evaluated the catalytic activities in these mutants.

As a result, the present inventors revealed that the catalytic activity was improved by substituting phenylalanine at position 140 in the OsHSL1 protein with a basic amino acid such as histidine. The present inventors also found that in an HIS1-homologous protein (the ZmHSL2 protein and the SbHSL1 protein) in other cultivars, the catalytic activity was improved by mutating an amino acid corresponding to position 140 of the OsHSL1 protein to a basic amino acid. Moreover, the present inventors found out that in *Arabidopsis thaliana* and a 4-HPPD inhibitor susceptible rice cultivar expressing the OsHSL1 protein in which position 140 was substituted with histidine, the resistance to the 4-HPPD inhibitor was improved. These findings have led to the completion of the present invention.

More specifically, the present invention is as follows:
<1> A method for producing an HSL protein with increased catalytic activity to oxidize a 4-HPPD inhibitor in a 2-oxoglutarate-dependent manner, comprising the step of
   mutating, in an HSL protein, position 140 of an amino acid sequence of SEQ ID NO: 4 or an amino acid corresponding to the position to a basic amino acid.

<2> A method for producing a plant with increased resistance to a 4-HPPD inhibitor, comprising the steps of:

(I) mutating, in an HSL protein of a plant cell, position 140 of an amino acid sequence of SEQ ID NO: 4 or an amino acid corresponding to the position to a basic amino acid; and (II) regenerating a plant from the plant cell in which amino acid mutation is introduced in the step (I).

<3> The production method according to <1> or <2>, wherein the basic amino acid is histidine, lysine, or arginine.

<4> A method for determining resistance of a plant to a 4-HPPD inhibitor, comprising:

detecting a nucleotide which codes for position 140 of an amino acid sequence of SEQ ID NO: 4 or an amino acid corresponding to the position in an HSL gene of a test plant; and if the nucleotide codes for a basic amino acid, determining that the test plant has resistance to a 4-HPPD inhibitor.

<5> A method for breeding a plant having increased resistance to a 4-HPPD inhibitor, the method comprising the steps of:

(a) crossing a plant cultivar having resistance to a 4-HPPD inhibitor with any cultivar;

(b) determining resistance of an individual obtained by the mating in the step (a) to a 4-HPPD inhibitor by the method according to <4>; and (c) selecting an individual determined to have resistant to the 4-HPPD inhibitor.

Advantageous Effects of Invention

According to the present invention, it is possible to increase the catalytic activity of an HSL protein to oxidize a 4-HPPD inhibitor in a 2-oxoglutarate-dependent manner by mutating, in the protein, position 140 of an amino acid sequence of SEQ ID NO: 4 or an amino acid corresponding to the position (hereinafter, also referred to simply as an "amino acid at position 140" to a basic amino acid.

In particular, in a case where the 4-HPPD inhibitor is benzobicyclon (hereinafter, also referred to as "BBC") and its hydrolysate (hereinafter, also referred to as "benzobicyclon hydrolysate" or "BBC-OH"), it is possible to further increase the catalytic activity to oxidize the inhibitor by further substituting position 204 or position 298, or an amino acid corresponding to the position each with another amino acid, in addition to the position 140.

Then, in the present invention, it is also possible to produce a plant with increased resistance to a 4-HPPD inhibitor by utilizing such a method for producing an HSL protein with increased catalytic activity to oxidize a 4-HPPD inhibitor in a 2-oxoglutarate-dependent manner.

Moreover, as described above, based on the finding that an amino acid at position 140 in an HSL protein is an amino acid that affects the catalytic activity, according to the present invention, it is also possible to determine resistance of a test plant to a 4-HPPD inhibitor by detecting a nucleotide which codes for an amino acid at position 140 in an HSL gene of the test plant. In addition, according to the present invention, it is also possible to provide a method for breeding a plant having increased resistance to a 4-HPPD inhibitor, utilizing the above method.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 10 is photographs showing results of observing growth conditions of *Arabidopsis thaliana* in which OsHSL1 protein mutants (the five-site mutant of V118I, F140H, L204F, S229T, and F298L, the four-site mutant of F140H, L204F, S229T, and F298L, the three-site mutant of F140H, or L204F, and F298L) are expressed in agar growth media containing 0.05 μM or 0.06 μM benzobicyclon (BBC), where lower right quarters in the respective two plates on the right side show results of observing growth conditions of *Arabidopsis thaliana* which was not transformed and arrows indicate individuals that took in green.

Figure 11:
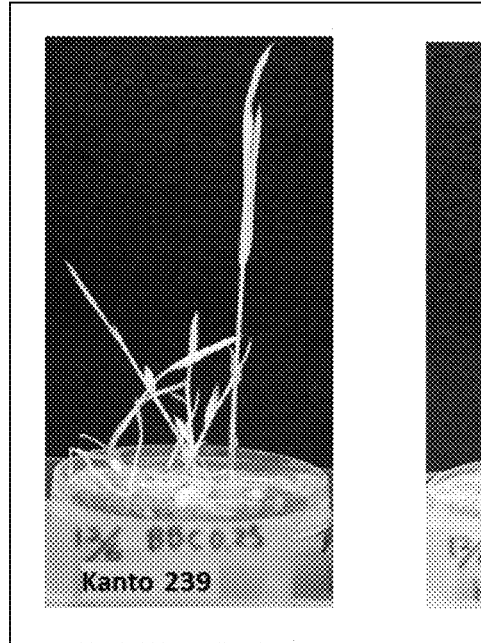
Figure 11:
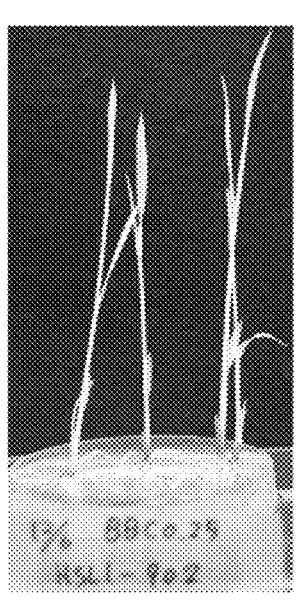
Figure 11:

FIG. 11 is photographs showing results of observing growth conditions of Yamadawara, which is a benzobicyclon-susceptible rice, Yamadawara in which a wild type of the OsHSL1 protein is expressed (in FIG. 11, "HSL1 (wild type) recombinant"), and Yamadawara in which a mutant (the single-site mutant of F140H) of the OsHSL1 protein is expressed (in FIG. 11, "mHSL1 (F140H) recombinant"), in BBC-containing MS media.

FIG. 12 is a table depicting 4-HPPD inhibitor decomposition activity of wild-type and variant proteins.

FIG. 13 is a table depicting 4-HPPD inhibitor decomposition activity of wild-type and variant proteins.

FIG. 14 is a table depicting 4-HPPD inhibitor decomposition activity of wild-type and variant proteins.

FIG. 15 is a table depicting 4-HPPD inhibitor decomposition activity of wild-type and variant proteins.

FIG. 16 is a table depicting 4-HPPD inhibitor decomposition activity of wild-type and variant proteins.

FIG. 17 is a table depicting 4-HPPD inhibitor decomposition activity of wild-type and variant proteins.

DESCRIPTION OF EMBODIMENTS

Method for Producing HSL Protein with Increased Catalytic Activity to Oxidize 4-HPPD Inhibitor in 2-Oxoglutarate-Dependent Manner The present invention provides a method for producing an HSL protein with increased catalytic activity to oxidize a 4-HPPD inhibitor in a 2-oxoglutarate-dependent manner, comprising the step of mutating, in an HSL protein, position 140 of an amino acid sequence of SEQ ID NO: 4 or an amino acid corresponding to the position to a basic amino acid.

Figure 1:
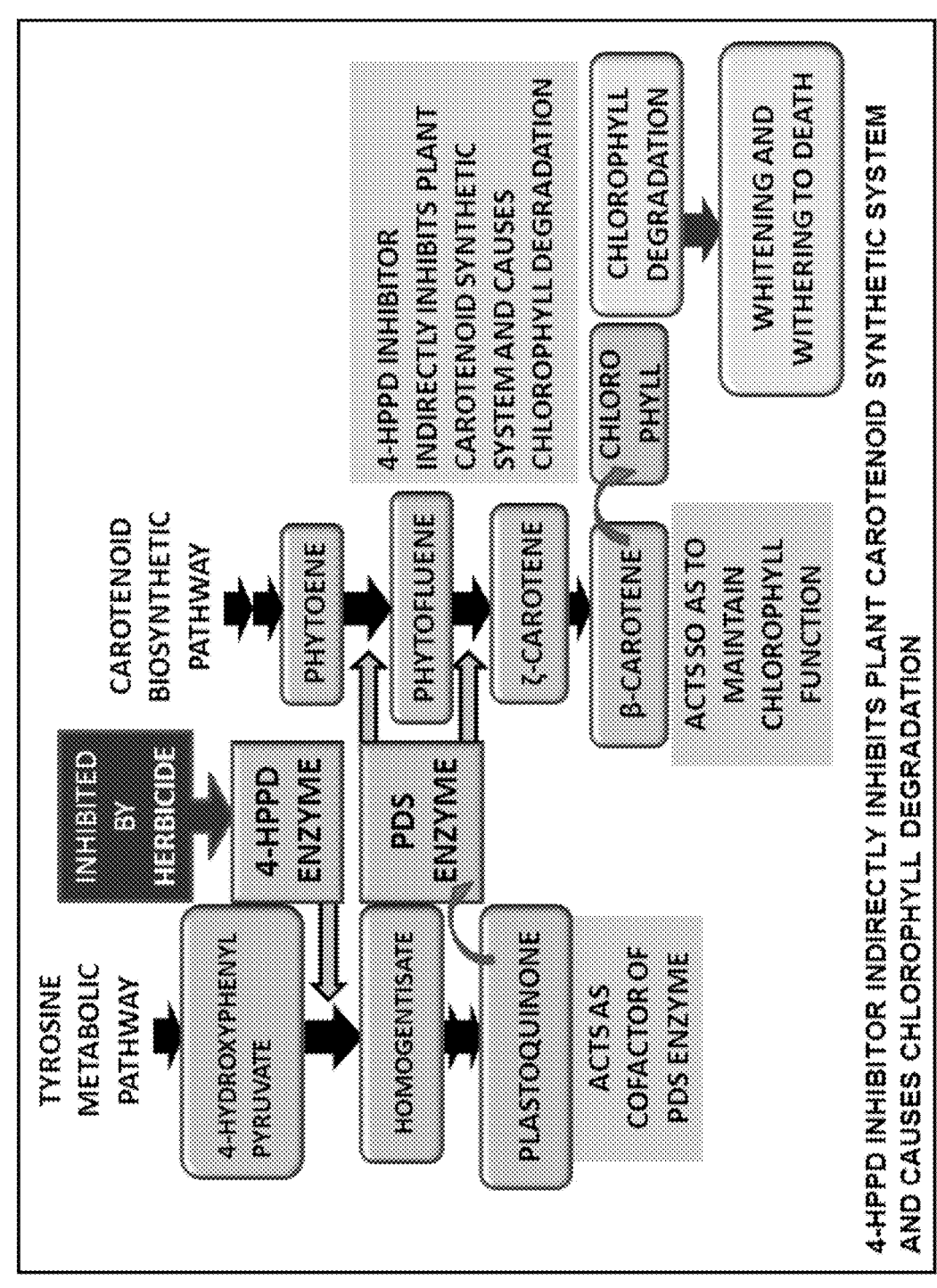
FIG. 1 is a diagram showing an outline and a relation between a tyrosine metabolism pathway and a carotenoid biosynthesis pathway and a 4-HPPD inhibitor.

The "4-HPPD inhibitors" in the present invention mean agents (4-HPPD inhibitors) that inhibit the function of 4-HPPD (4-hydroxyphenylpyruvate dioxygenase, EC Number: 1.13.11.27, 1.14.2.2). As shown in FIG. 1, the 4-HPPD inhibitors inhibit the function of 4-HPPD and thus indirectly inhibit the carotenoid synthesis system to cause chlorophyll degradation, whitening plants and withering the plants to death.

The "4-HPPD inhibitors" in the present invention is classified into (1) cyclohexanedione type, (2) pyrazole type, (3) bicyclo type, (4) isoxazole type (see "From Pesticides to Agrobioregulators—disease, pest, and weed controls at present and in the future", Japan, CMC Publishing Co., Ltd., December, 2009).

(1) The cyclohexanedione type includes, for example, tefuryltrione (CAS registry number: 473278-76-1), sulcotrione (CAS registry number: 99105-77-8), mesotrione (CAS registry number: 104206-82-8), tembotrione (CAS registry number: 335104-84-2), lancotrione (CAS registry number: 1486617-21-3), and 2-[2-nitro-4-(trifluoromethyl)benzoyl]cyclohexane-1, 3-di one (Nitisinone, NTBC, CAS registry number: 104206-65-7).

(2) The pyrazole type includes, for example, pyrazolynate (CAS registry number: 58011-68-0), benzofenap (CAS registry number: 82692-44-2), pyrazoxyfen (CAS registry number: 71561-11-0), topramezone (CAS registry number: 210631-68-8), and pyrasulfotole (CAS registry number: 365400-11-9).

(3) The bicyclo type includes, for example, benzobicyclon (BBC, CAS registry number: 156963-66-5), benzobicyclon hydrolysate (BBC-OH, CAS registry number: 126656-88-0), and bicyclopyrone (CAS registry number: 352010-68-5).

(4) The isoxazole type includes, for example, isoxaflutole (CAS registry number: 141112-29-0).

The 4-HPPD inhibitor for which the present invention has been made is preferably a 4-HPPD inhibitor of the cyclohexanedione type or the bicyclo type such as benzobicyclon (BBC) or a hydrolysate thereof (benzobicyclon hydrolysate, BBC-OH), tefuryltrione, sulcotrione, mesotrione, tembotrione, lancotrione, bicyclopyrone, or NTBC, more preferably BBC, BBC-OH, tefuryltrione, sulcotrione, mesotrione, or tembotrione, further preferably BBC, BBC-OH, or tefuryltrione, and particularly preferably BBC or BBC-OH.

Note that whether a certain compound has the 4-HPPD inhibitory activity may be determined by analyzing whether the generation of homogentisic acid from 4-hydroxyphenylpyruvic acid, which is promoted by the 4-HPPD enzyme, is suppressed in the presence of the compound (see, for example, the descriptions of Schulz, A. Ort, O. Beyer, P. Kleinig, H. (1993), FEBS Lett., 318, 162-166, and Secor, J. (1994), Plant Physiol., 106, 1429-1433).

The "catalytic activity" in the present invention means, as shown in the following reaction formula, the activity to catalyze the oxidation reaction of a 4-HPPD inhibitor ("R" in the following reaction formula), which serves as a substrate, in a 2-oxoglutarate ("2OG" in the following reaction formula)-dependent manner.

$$R + 2OG + O_2 \rightarrow RO + succinic\ acid + CO_2$$

Note that this reaction involves the generation of succinic acid and carbon dioxide resulting from the decarboxylation of 2OG.

The HSL protein the catalytic activity of which is increased in the present invention means a protein (HSL protein) having a high homology with a HIS1 protein (typically, a protein having an amino acid sequence of SEQ ID NO: 2). The high homology is a sequence homology of at least 60% or more, and preferably 80% or more (for example, 85%, 90%, 95%, 97%, or 99% or more). The sequence homology may be determined utilizing the BLASTP (amino acid level) program (Altschul et al. J. Mol. Biol., 215: 403-410, 1990). This program is based on the algorithm blast by Karlin and Altschul (Proc. Natl. Acad. Sci. USA, 87: 2264-2268, 1990, Proc. Natl. Acad. Sci. USA, 90: 5873-5877, 1993). When an amino acid sequence is analyzed using the BLASTP, the parameters are set at, for example, score=50, wordlength=3. On the other hand, when an amino acid sequence is analyzed using the Gapped BLAST program, the analysis may be conducted as described in Altschul et al. (Nucleic Acids Res. 25: 3389-3402, 1997). Moreover, when both of the BLAST and the Gapped BLAST program are used, default parameters of each program are used. Specific procedures of these analyzing methods are known.

The source of the "HSL protein" according to the present invention is not particularly limited as long as the source is a plant, which includes, for example, rice, barley, wheat, corn, and sorghum. More specifically, the rice-derived HSL protein includes an OsHSL1 protein (typically, a protein having an amino acid sequence of SEQ ID NO: 4), an OsHSL2 protein (typically, a protein having an amino acid sequence of SEQ ID NO: 6), and the like. The barley-derived HSL protein includes an HvHSL1 protein (typically, a protein having an amino acid sequence of SEQ ID NO: 8), an HvHSL2 protein (typically, a protein having an amino acid sequence of SEQ ID NO: 10), an HvHSL3 protein (typically, a protein having an amino acid sequence of SEQ ID NO: 12), and the like. The wheat-derived HSL protein includes a TaHSL1 protein (typically, a protein having an amino acid sequence of SEQ ID NO: 14), a TaHSL2 protein (typically, a protein having an amino acid sequence of SEQ ID NO: 16), and the like. The corn-derived HSL protein includes a ZmHSL1 protein (typically, a protein having an amino acid sequence of SEQ ID NO: 18), a ZmHSL2 protein (typically, a protein having an amino acid sequence of SEQ ID NO: 20), and the like. The sorghum-derived HSL protein includes a SbHSL1 protein (typically, a protein having an amino acid sequence of SEQ ID NO: 22) and the like. However, the HSL protein according to the present invention is not limited to these. In addition, the amino acid sequence of a protein also changes as a result of mutation of a nucleotide sequence in nature (that is, non-artificially). Hence, it should be appreciated that the target of the present invention encompasses not only the proteins having the above-described typical amino acid sequences but also such natural mutants.

In addition, the "basic amino acid" with which position 140 of an amino acid sequence of SEQ ID NO: 4 or an amino acid corresponding to the position in the above-described HSL protein is substituted in order to increase the catalytic activity includes, for example, histidine, lysine, and arginine, and is preferably histidine from the viewpoint that histidine allows the catalytic activity to be more easily increased.

Moreover, in the present invention, mutation may be introduced into an amino acid at another position instead of mutating position 140 of an amino acid sequence of SEQ ID NO: 4 or an amino acid corresponding to the position to a basic amino acid. Such "mutation" means that one or a plurality of amino acids of an HSL protein are substituted, deleted, added, and/or inserted at positions other than the position 140 of the amino acid sequence of SEQ ID NO: 4 or the portion corresponding to the position. Here, the "plurality" is not particularly limited but is normally 2 to 40, preferably 2 to 30, more preferably 2 to 20, and further preferably 2 to 10 (for example, 2 to 8, 2 to 4, or 2 to 2)

The mutation to be introduced into another portion is not particularly limited. However, from the viewpoint that the catalytic activity to oxidize BBC or BBC-OH is more easily increased, it is preferable that at least one amino acid out of position 204 of the amino acid sequence of SEQ ID NO: 4 or an amino acid corresponding to the position and position 298 of the amino acid sequence of SEQ ID NO: 4 or an amino acid corresponding to the position be each substituted with another amino acid, and it is more preferable that these 2 positions be each substituted with another amino acid. In addition, such "another amino acid" is also not particularly limited. However, from the same viewpoint, it is preferable that position 204 of the amino acid sequence of SEQ ID NO: 4 or an amino acid corresponding to the position be substituted with phenylalanine, and it is preferable that position 298 of the amino acid sequence of SEQ ID NO: 4 or an amino acid corresponding to the position be substituted with leucine.

Note that in the present invention, the "corresponding position" is a position that is matched up with position 140 or the like of the amino acid sequence of SEQ ID NO: 4 or the like of the amino acid sequence of SEQ ID NO: 4 when the amino acid sequence of SEQ ID NO: 4 and an amino acid sequence of another SL protein are aligned with each other utilizing amino acid sequence analysis software (GENETYX-MAC, Sequencher, or the like), BLAST (blast.ncbi.nlm.nih.gov/Blast.cgi), CLUSTALW (genome.jp/tools/clustalw/).

In addition, mutagenesis in an HSL protein may be conducted by a mutagenesis method at an amino acid sequence level or by a mutagenesis method at a nucleotide sequence level.

The mutagenesis method at an amino acid sequence level includes a method including chemically synthesizing the mutant using a commercially-available peptide synthesizer based on the amino acid sequence of the HSL protein in which mutation has been introduced at a desired position.

In addition, the mutagenesis at a nucleotide sequence level includes, for example, a site-directed mutagenesis method, a genome editing method, a chemical DNA synthesis method based on nucleotide sequence information coding for an HSL protein in which mutation has been introduced at a desired position. Then, based on the nucleotide prepared by such a mutagenesis method, it is possible to obtain an HSL protein or the like in which position 140 is substituted with a basic amino acid, by utilizing a biological synthesis system or a cell-free protein synthesis system.

The biological synthesis system includes cells such as yeast, plant cells, insect cells, and animal cells. By introducing, into such cells, a cassette (a plasmid vector or the like) capable of expressing a nucleotide coding for the HSL protein or the like in the cells, it is possible to prepare the protein or the like.

In addition, the cell-free protein synthesis system includes, for example, wheat germ-derived, *Escherichia coli*-derived, rabbit reticulocyte-derived, and insect cell-derived synthesis systems. By adding, to such a synthesis system (a cell extract or the like), a cassette (a plasmid vector or the like) capable of expressing a nucleotide coding for the HSL protein or the like in the synthesis system, it is possible to prepare the protein or the like.

Note that among such synthesis systems, a wheat germ-derived cell-free protein synthesis system is preferable from the viewpoint that it is easy to prepare an HSL protein having the catalytic activity as shown in Examples described later. In addition, a synthesis system using tris(2-carboxy-ethyl)phosphine (TCEP) as a reducing agent is preferable from the viewpoint of suppressing influence on the catalytic activity of an HSL protein.

In addition, whether the catalytic activity has been increased by the above-described mutagenesis can be evaluated by, for example: processing a 4-HPPD inhibitor in the presence of an HSL protein in which mutation has been introduced, divalent iron ions, 2-oxoglutarate, and oxygen; then directly measuring the amount of an oxide of the 4-HPPD inhibitor or measuring the amount of a product (degradant) generated during the oxidation by means of a high-performance liquid chromatography analysis; and comparing the measured amount with the amount in the HSL protein before the introduction of the mutation, as shown in Examples described later. Moreover, as shown in the above-described reaction formula, such reaction also generates not only an oxide of the 4-HPPD inhibitor but also succinic acid at the same time. For this reason, it is also possible to determine whether the catalytic activity has been increased, by measuring the amount of succinic acid generated in the presence of an HSL protein in which mutation has been introduced and comparing the measured amount with the amount in the HSL protein before the introduction of the mutation.

Method for Producing Plant with Increased Resistance to 4-HPPD Inhibitor

As described above, by substituting position 140 of an HSL protein with a basic amino acid, it is possible to increase the activity to oxidize and decompose the 4-HPPD inhibitor, and in turn also to improve resistance to the 4-HPPD inhibitor in a plant in which the protein has been expressed, as shown in Examples described later.

Hence, the present invention can also provide a method for producing a plant with increased resistance to a 4-HPPD inhibitor, comprising the steps of:

(I) mutating, in an HSL protein of a plant cell, position 140 of an amino acid sequence of SEQ ID NO: 4 or an amino acid corresponding to the position to a basic amino acid; and (II) regenerating a plant from the plant cell in which amino acid mutation is introduced in the step (I).

The plant whose resistance to a 4-HPPD inhibitor can be increased by the method according to the present invention is not particularly limited, and includes, for example, *Poaceae* plants such as rice, barley, wheat, sorghum, corn, and creeping bentgrass, *Brassicaceae* plants such as *Arabidopsis thaliana, Solanaceae* plants such as tomato, *Fabaceae* plants such as soybean, alfalfa, and *Lotus japonicas, Malvaceae* plants such as cotton plant, and *Chenopodiaceae* plants such as sugar beet. Among these plants, 4-HPPD inhibitor-susceptible cultivars are particularly preferable as a target to which the present invention is applied to increase resistance to a 4-HPPD inhibitor. A 4-HPPD inhibitor-susceptible rice cultivar includes, for example, Yamadawara (Kanto 239), Habataki, Takanari, Momiroman, Mizuhochikara, Ruriaoba, Odorokimochi, Hyogo-ushi-wakamaru, Kasalath, and the like, but is not limited thereto.

The plant cell of the present invention includes, besides culture cells, cells in plants. Further, the plant cell of the present invention includes plant cells in various forms, for example, suspended culture cells, protoplasts, leaf sections, calli, immature embryos, pollens, and the like.

A method for mutating, in an HSL protein of a plant cell, an amino acid at position 140 to a basic amino acid includes genome editing. In such genome editing, a person skilled in the art can surely substitute an amino acid at position 140 in a plant cell with a basic amino acid, for example, by using fusion proteins such as ZFNs (U.S. Pat. Nos. 6,265,196, 8,524,500, and 7,888,121, European Patent No. 1720995), TALENs (U.S. Pat. Nos. 8,470,973 and 8,586,363), PPR (pentatricopeptide repeat) associated with a nuclease domain (Nakamura et al., Plant Cell Physiol 53: 1171-1179 (2012)), and complexes of guide RNAs and proteins such as CRISPR-Cas9 (U.S. Pat. No. 8,697,359, International Publication No. WO2013/176772), CRISPR-Cpf1 (Zetsche B. et al., Cell, 163 (3): 759-71, (2015)), and Target-AID (K. Nishida et al., Targeted nucleotide editing using hybrid prokaryotic and vertebrate adaptive immune systems, Science, DOI: 10. 1126/science. aaf 8729, (2016)).

In addition, another method for mutating, in an HSL protein of a plant cell, an amino acid at position 140 to a basic amino acid includes a genetic recombination method. In this method, a nucleotide coding for an HSL protein in which an amino acid at position 140 has been substituted with a basic amino acid is introduced into a plant cell, which causes homologous recombination between the nucleotide and an HSL gene on the genome of the cell, substituting the amino acid at the position 140 with the basic amino acid in the cell (what is termed as gene targeting). Note that a person skilled in the art can prepare the nucleotide, for example, by means of a method described in the above-described "mutagenesis at a nucleotide sequence level." In addition, the introduction of the nucleotide into a plant cell can be conducted as appropriate, for example, by using a method described in a method of regenerating a plant, which is described later.

Moreover, as a matter of course, in the method for producing a plant according to the present invention as well, mutation may be introduced not only into position 140 or an amino acid corresponding to the position but also into an amino acid at another position. As the mutation at another position, for example, from the viewpoint that the resistance to BBC or BBC-OH is more easily increased, it is preferable that at least one amino acid out of position 204 of the amino acid sequence of SEQ ID NO: 4 or an amino acid corresponding to the position and position 298 of the amino acid sequence of SEQ ID NO: 4 or an amino acid corresponding to the position be each substituted with another amino acid, and it is more preferable that these 2 positions be each substituted with another amino acid. In addition, such "another amino acid" is also not particularly limited. However, from the same viewpoint, it is preferable that position 204 of the amino acid sequence of SEQ ID NO: 4 or an amino acid corresponding to the position be substituted with phenylalanine, and it is preferable that position 298 of the amino acid sequence of SEQ ID NO: 4 or an amino acid corresponding to the position be substituted with leucine.

In the present invention, the regeneration of a plant from a plant cell in which amino acid mutation has been introduced can be conducted by means of a method publicly known to a person skilled in the art depending on the type of the plant cell.

For example, several techniques of the procedure for producing regenerated rice plants have been already established, such as a method in which a gene is introduced into protoplasts using polyethylene glycol and a plant is regenerated (Datta, S. K. In Gene Transfer To Plants (Potrykus I and Spangenberg Eds.) pp 66-74, 1995); a method in which a gene is introduced into protoplasts using electric pulse and a plant is regenerated (Toki et al. Plant Physiol. 100, 1503-1507, 1992); a method in which a gene is directly introduced into cells by a particle gun method and a plant is regenerated (Christou et al. Bio/technology, 9: 957-962, 1991); and a method in which a gene is introduced using *Agrobacterium* and a plant is regenerated (Hiei et al. Plant J. 6: 271-282, 1994). These are widely used in the technical field of the present invention.

Moreover, the procedure for producing regenerated barley plants includes methods described in Tingay et al. (Tingay S. et al. Plant J. 11: 1369-1376, 1997), Murray et al. (Murray F et al. Plant Cell Report 22: 397-402, 2004), and Travalla et al. (Travalla S et al. Plant Cell Report 23: 780-789, 2005).

In addition, the procedure for producing regenerated wheat plants includes, for example, a method described in "Taiich Ogawa, Japanese Journal of Pesticide Science, 2010, vol. 35, no. 2, pp 160 to 164".

Moreover, the procedure for producing regenerated corn plants includes, for example, methods described in "Ishida Y. et al., Nat Protoc., 2007, vol. 2, no. 7, pp 1614 to 1621", "Hiei Y. et al., Front Plant Sci., Nov. 7, 2014; 5: 628. doi: 10. 3389/fpls. 2014. 00628. eCollection 2014.", and "Hiei et al., Breeding Science Study, 2000, pp 205 to 213".

As the method for regenerating sorghum plants, preferably used are, for example, a method in which a gene is introduced into immature embryos or calli by an *Agrobacterium* method or a particle gun method and a plant is regenerated; and a method in which pollens having a gene introduced therein using ultrasound are used for pollination (J. A. Able et al., In Vitro Cell. Dev. Biol. 37: 341-348, 2001, A. M. Casas et al., Proc. Natl. Acad. Sci. USA 90: 11212-11216, 1993, V. Girijashankar et al., Plant Cell Rep 24: 513-522, 2005, J. M. JEOUNG et al., Hereditas 137: 20-28, 2002, V Girijashankar et al., Plant Cell Rep 24 (9): 513-522, 2005, Zuo-yu Zhao et al., Plant Molecular Biology 44: 789-798, 2000, S. Gurel et al., Plant Cell Rep 28 (3): 429-444, 2009, Z Y Zhao, Methods Mol Biol, 343: 233-244,2006, A K Shrawat and H Lorz, Plant Biotechnol J, 4 (6): 575-603, 2006, D Syamala and P Devi Indian J Exp Biol, 41 (12): 1482-1486, 2003, and Z Gao et al., Plant Biotechnol J, 3 (6): 591-599, 2005).

Further, the procedure for *Arabidopsis thaliana* includes a method by Akama et al. (Akama et al. Plant Cell Reports 12: 7-11, 1992). In the present invention, these methods can be preferably used.

In addition, also regarding other plants, transformation and regeneration to the plants can be conducted using a method described in Tabei et al., (Tabei Y. Ed., "Protocols of Plant Transformation, Kagaku-Dojin Publishing Company, INC, published on Sep. 20, 2012).

Once a plant with increased resistance to a 4-HPPD inhibitor is obtained, it is possible to obtain a progeny from the plant by sexual reproduction or asexual reproduction. In addition, propagation materials (for example, seeds, fruits, spikes, stubs, calli, protoplasts, and the like) are obtained from the plant or a progeny or a clone thereof, from which the plant can also be produced in mass.

In addition, whether the resistance of the plant to a 4-HPPD inhibitor has been improved by the above method can be determined, for example, by examining whether the resistance has been improved in the produced plant by introducing the above-described mutation into the plant, as described in Examples described later. Specifically, with the concentration of a 4-HPPD inhibitor with which a plant before mutagenesis is whitened (for example, 0.05 μM or more in the case where *Arabidopsis thaliana* (*A. thaliana*: ecotype Columbia) is used), if a plant in which the above-described amino acid mutation has been introduced can be grown without being whitened, it can be determined that the resistance of the plant has been increased.

Although the preferred embodiment of the method for producing a plant with increased resistance to a 4-HPPD inhibitor according to the present invention has been described so far, the method for producing a plant according to the present invention is not limited to the above-described embodiment.

As shown in Examples described later, even when homologous recombination does not occur in the above-described genetic recombination method (for example, even when the nucleotide is inserted into the genome of the plant cell at random), it is possible to produce a plant with increased resistance to a 4-HPPD inhibitor by introducing the nucleotide into the plant cell.

Hence, the present invention can also provide a method for producing a plant with increased resistance to a 4-HPPD inhibitor, comprising the steps of:

(I) introducing a nucleotide coding for an HSL protein in which an amino acid at position 140 is substituted with a basic amino acid into a plant cell; and (II) regenerating a plant from the plant cell in which the nucleotide is introduced in the step (I).

As described above, a person skilled in the art can prepare the nucleotide, introduce the nucleotide into a plant cell, and obtain a plant from the plant cell, using publicly-known methods as appropriate. In addition, as described above, also in this production method using the genetic recombination method as well, mutation may be introduced not only into position 140 or an amino acid corresponding to the position but also into an amino acid at another position.

Moreover, in this method, the plant from which the nucleotide is derived and the plant from which the cell is derived may be of the same cultivar (for example, both are rice) as in Example 6 described later. Alternatively, the plant from which the nucleotide is derived and the plant from which the cell is derived may be different cultivars (for example, the former is derived from rice and the latter is derived from *Arabidopsis thaliana*) as in Example 5 described later.

Method for Determining Resistance of Plant to 4-HPPD Inhibitor

As shown in Examples described later, the amino acid at position 140 of an HSL protein greatly contributes to the resistance to a 4-HPPD inhibitor. Hence, the present invention also provides a method for determining resistance of a plant to a 4-HPPD inhibitor, comprising: detecting a nucleotide which codes for position 140 of an amino acid sequence of SEQ ID NO: 4 or an amino acid corresponding to the position in an HSL gene of a test plant; and if the nucleotide codes for a basic amino acid, determining that the test plant has resistance to a 4-HPPD inhibitor.

The preparation of a nucleotide from a test plant in the determination method of the present invention can be conducted using a conventional method, for example, the CTAB method. As the plant for preparing a nucleotide, not only grown plants but also seeds or infant plants may be used.

Whether the nucleotide obtained in this way has coded for the amino acid at position 140 of SEQ ID NO: 4 in an HSL gene can be detected by conducting sequencing. Moreover, besides such direct determination of a nucleotide sequence, the analysis can be made indirectly by various methods. Such methods include, for example, the PCR-SSCP (single-strand conformation polymorphism) method, the RFLP method and the PCR-RFLP method utilizing the restriction fragment length polymorphism (RFLP), the denaturant gradient gel electrophoresis (DGGE), the allele-specific oligonucleotide (ASO) hybridization method, and the ribonuclease A mismatch cleavage method.

Method for Breeding Plant According to Present Invention

The present invention provides a method for breeding a plant having increased resistance to a 4-HPPD inhibitor. This breeding method comprises the steps of: (a) crossing a plant cultivar having resistance to a 4-HPPD inhibitor with any cultivar; (b) determining resistance of an individual obtained by the mating in the step (a) to a 4-HPPD inhibitor by the above-described <Method for Determining Resistance of Plant to 4-HPPD Inhibitor>; and (c) selecting an individual determined to have resistant to the 4-HPPD inhibitor.

The "any plant cultivar" to be crossed with a plant cultivar having resistance to a 4-HPPD inhibitor includes, for example, a 4-HPPD inhibitor-susceptible cultivar and an individual obtained by crossing a 4-HPPD inhibitor-resistant cultivar and a 4-HPPD inhibitor-susceptible cultivar, but is not limited to these.

Utilizing the breeding method according to the present invention makes it possible to select a 4-HPPD inhibitor-resistant or susceptible cultivar at the stages of seeds and infant plants and thus makes it possible to breed a cultivar having these characters in a short period of time.

Although the preferred embodiments of the present invention have been described so far, the present invention is not limited to the above-described embodiments.

As shown in Examples described later, when BBC or BBC-OH is used as a substrate for a 4-HPPD inhibitor, the catalytic activity to oxidize the agent can be increased also by substituting position 204 and/or position 298 of an HSL protein each with another amino acid (for example, substituting position 204 with phenylalanine and substituting position 298 with leucine) without substituting position 140 with a basic amino acid. In addition, the catalytic activity to oxidize not only BBC and BBC-OH but also sulcotrione, mesotrione, and tembotrione can be increased by substituting position 204 and position 298 of an HSL protein each with another amino acid (for example, substituting position 204 with phenylalanine and substituting position 298 with leucine).

Hence, the present invention provides the following.

<6> A method for producing an HSL protein with increased catalytic activity to oxidize a 4-HPPD inhibitor in a 2-oxoglutarate-dependent manner, comprising the step of: mutating, in an HSL protein, amino acids at position 204 or a portion corresponding to the position and/or position 298 or a portion corresponding to the position of an amino acid sequence of SEQ ID NO: 4 each to another amino acid.

<7> A method for producing a plant with increased resistance to a 4-HPPD inhibitor, comprising the steps of:

(I) mutating, in an HSL protein of a plant cell, amino acids at position 204 or a portion corresponding to the position and/or position 298 or a portion corresponding to the position of an amino acid sequence of SEQ ID NO: 4 each to another amino acid; and (II) regenerating a plant from the plant cell in which amino acid mutation is introduced in the step (I).

<8> A method for determining resistance of a plant to a 4-HPPD inhibitor, comprising: detecting a nucleotide which codes for amino acids at position 204 or a portion corresponding to the position and/or position 298 or a portion corresponding to the position of SEQ ID NO: 4 in an HSL gene of a test plant; and if the nucleotide codes for phenylalanine at position 204 or a portion corresponding to the position and/or for leucine at position 298 or a portion corresponding to the position, determining that the test plant has resistance to a 4-HPPD inhibitor.

<9> A method for breeding a plant having increased resistance to a 4-HPPD inhibitor, the method comprising the steps of:

(a) crossing a plant cultivar having resistance to a 4-HPPD inhibitor with any cultivar;

(b) determining resistance of an individual obtained by the mating in the step (a) to a 4-HPPD inhibitor by the method according to <8>; and (c) selecting an individual determined to have resistance to the 4-HPPD inhibitor.

On the other hand, when tefuryltrione is used as a substrate for a 4-HPPD inhibitor, the catalytic activity to oxidize the agent can be reduced by substituting position 204 and/or position 298 of an HSL protein each with another amino acid (for example, substituting position 204 with phenylalanine and substituting position 298 with leucine) as shown in Examples described later.

Hence, the present invention also provides the following.

<10> A method for producing an HSL protein having reduced catalytic activity to oxidize tefuryltrione in a 2-oxoglutarate-dependent manner, the method comprising the step of:

mutating, in an HSL protein, amino acids at position 204 or a portion corresponding to the position and/or position 298 or a portion corresponding to the position of an amino acid sequence of SEQ ID NO: 4 each to another amino acid.

<11> A method for producing a plant having reduced resistance to benzobicyclon, benzobicyclon hydrolysate, or sulcotrione, the method comprising the steps of:

(I) mutating, in an HSL protein of a plant cell, amino acids at position 204 or a portion corresponding to the position and/or position 298 or a portion corresponding to the position of an amino acid sequence of SEQ ID NO: 4 each to another amino acid; and (II) regenerating a plant from the plant cell in which amino acid mutation is introduced in the step (I).

EXAMPLES

Although the present invention is described in more detail based on Examples below, the present invention is not limited to the following Examples.

The present inventors previously found that a gene (HIS1) rice has and a homologous gene (HSL1 gene) thereof contribute to resistance or susceptibility to a 4-HPPD inhibitor. The present inventors also found that a plant with increased resistance or susceptibility to a 4-HPPD inhibitor could be produced by utilizing these genes, and further found that genes having a high homology with the HIS1 gene of rice also exist in barley, sorghum, corn, and the like (PTL 1).

In addition, it has been surmised by the present inventors that the HIS1 and the OsHSL1 are 2-oxoglutarate-dependent dioxygenases (2OGDs), which are oxidases dependent on divalent iron ions and 2-oxoglutarate according to the amino acid motif search. The 2OGD is a protein containing non-heme iron ions, and is a soluble protein that locally exists in cytoplasms of plants. The 2OGD requires 2-oxoglutarate (2OG) and an oxygen molecule as co-substrates and requires a divalent iron ion as a cofactor. As described below, the 2OGD catalyzes the oxidation of the substrate ("R" in the following reaction formula) and this catalysis involves generation of succinic acid and carbon dioxide as a result of decarboxylation of 2OG.

$$R+2OG+O_2 \rightarrow RO+\text{succinic acid}+CO_2.$$

The catalytic center of each individual 2OGD takes a double-stranded β helix structure and has a preserved sequence motif, His-Xaa-Asp/Glu-(Xaa) n-His (SEQ ID NO: 23). This motif binds to a divalent iron ion to form a catalytic triad. The 2OGDs can be seen in from bacteria, animals, through plants, and have a wide variety of functions such as DNA modification, collagen synthesis, production of antibiotics, synthesis of plant hormones, and stress response. From gene information searching, it was predicted that there are 114 types from rice and 130 types from *Arabidopsis thaliana* (Kawai et al., Evolution and diversity of the 2-oxoglutarate-dependent dioxygenase superfamily in plants. The Plant Journal vol. 78 pp. 328-343, 2014).

Example 1

Evaluation on 4-HPPD Inhibitor Decomposition Activity of HIS1 Protein and Homologous Protein thereof (OsHSL1 Protein)

In view of the above, the present inventors synthesized HIS1 and a homologous protein thereof by a cell-free protein synthesis method using a wheat germ extract described later and evaluated the herbicide (4-HPPD inhibitor) decomposition activity of these.

Note that in the beginning, the present inventors attempted to synthesize an HIS1 protein and the like using protein expression systems of *Escherichia coli* (the pET system, the pCold system, and the like), but not a cell-free protein synthesis method using a wheat germ extract. However, only insoluble HIS1 proteins were produced by any of the pET system, the pCold system, and the like, and the activity was not recovered even for solubilized proteins. For this reason, HIS1 proteins were synthesized by a cell-free protein synthesis system using a wheat germ extract to obtain soluble HIS1 proteins.

Then, the decomposition reaction of a 4-HPPD inhibitor was examined in the presence of divalent iron ions, 2-oxoglutarate, and molecular oxygen in a test tube by a method described later using the HIS1 protein prepared by this cell-free protein synthesis system.

Here, in commercially-available wheat germ extracts, dithiothreitol (DTT) is used as a reducing agent and a protein synthesizing reaction liquid also contains DTT. It was confirmed in advance by liquid chromatography that under the coexistence of divalent iron ions and ascorbic acid, which is a stabilizer for the divalent iron ions, DTT generated radical compounds and secondarily affected the enzyme reaction of HIS1 proteins. For this reason, in the present Example, an unreported protein synthesizing reaction system using Tris (2-carboxyethyl) phosphine (TCEP) as a reducing agent instead of DTT was newly constructed, with which the synthesis of HIS1 proteins and the like was conducted to examine the 4-HPPD inhibitor decomposition activity of these. The decomposition activity was analyzed on the reaction liquid of the protein and the 4-HPPD inhibitor using a high-performance liquid chromatography (mobile phase; 0.5% acetic acid water:acetonitrile=65:35, flow rate; 1 mL/min, feeding; isocratic, column; CAPCELL PAK ADME S5).

Figure 2:
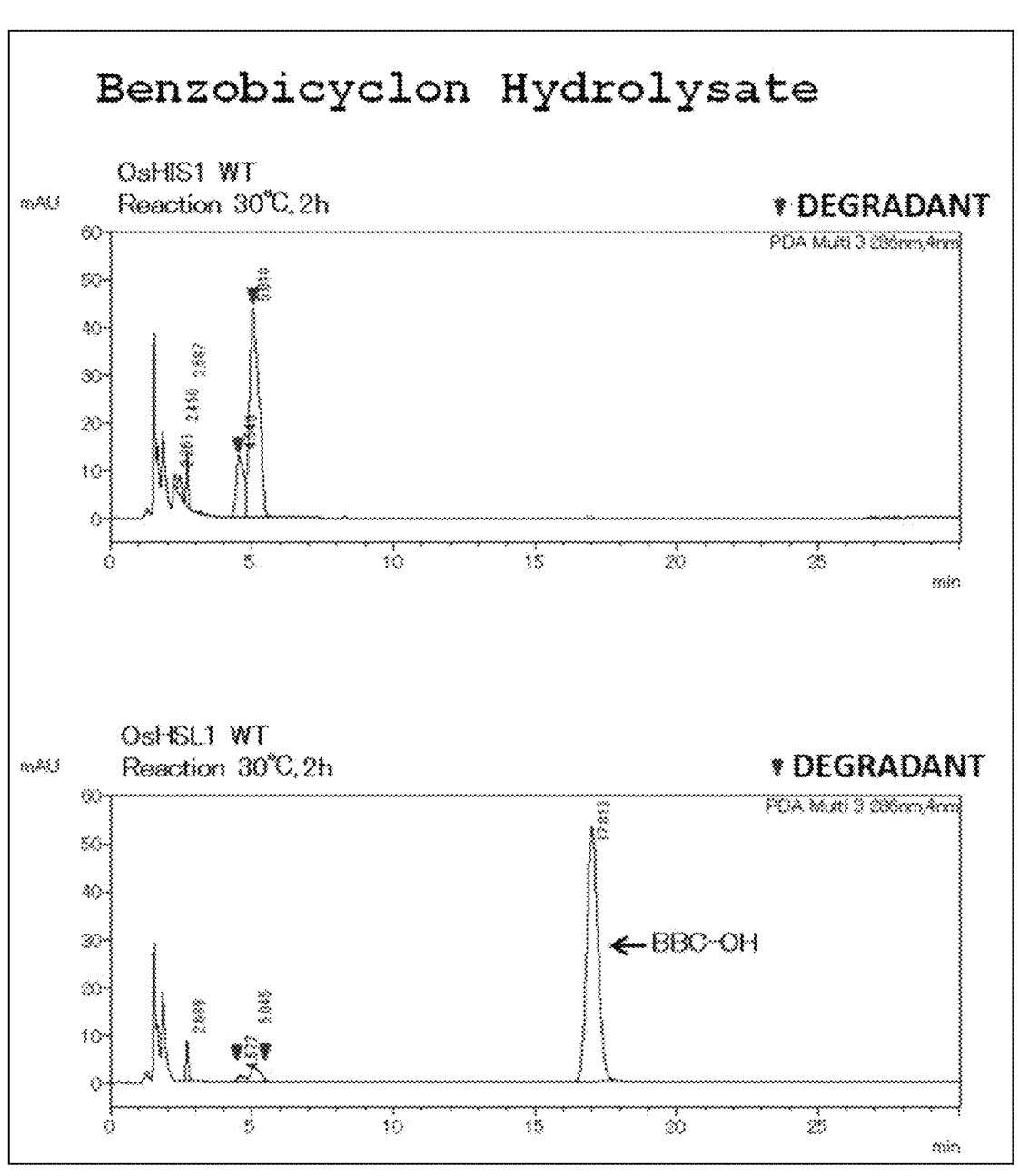
FIG. 2 is spectra showing results of analyzing benzobicyclon hydrolysate (BBC-OH) decomposition activities of an HIS1 protein and an OsHSL1 protein using high-performance liquid chromatography, where triangles each indicate a peak derived from a degradant of BBC-OH.
Figure 3:
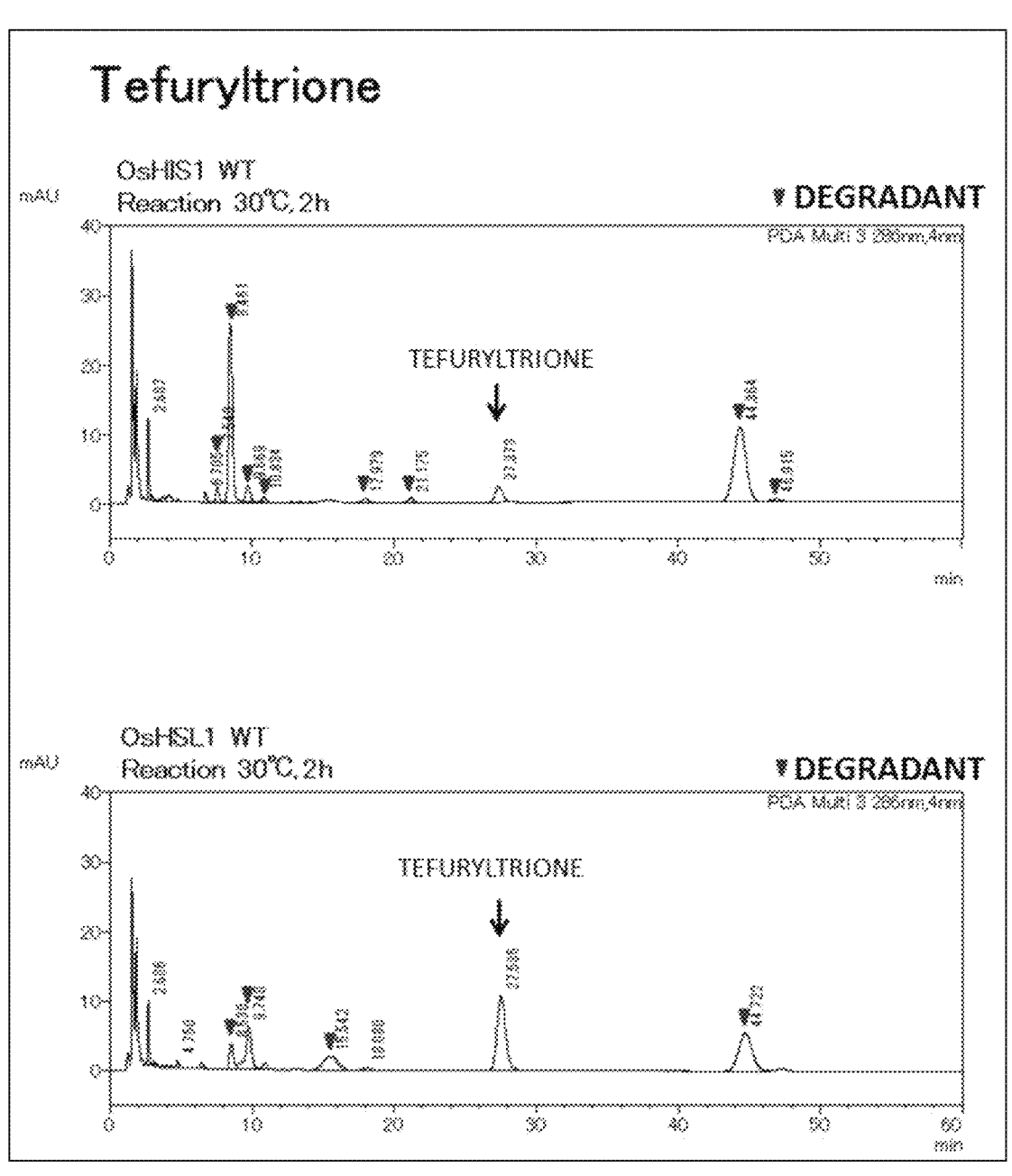
FIG. 3 is spectra showing results of analyzing tefuryltrione decomposition activities of the HIS1 protein and the OsHSL1 protein using high-performance liquid chromatography, where triangles each indicate a peak derived from a degradant of tefuryltrione.
Figure 4:
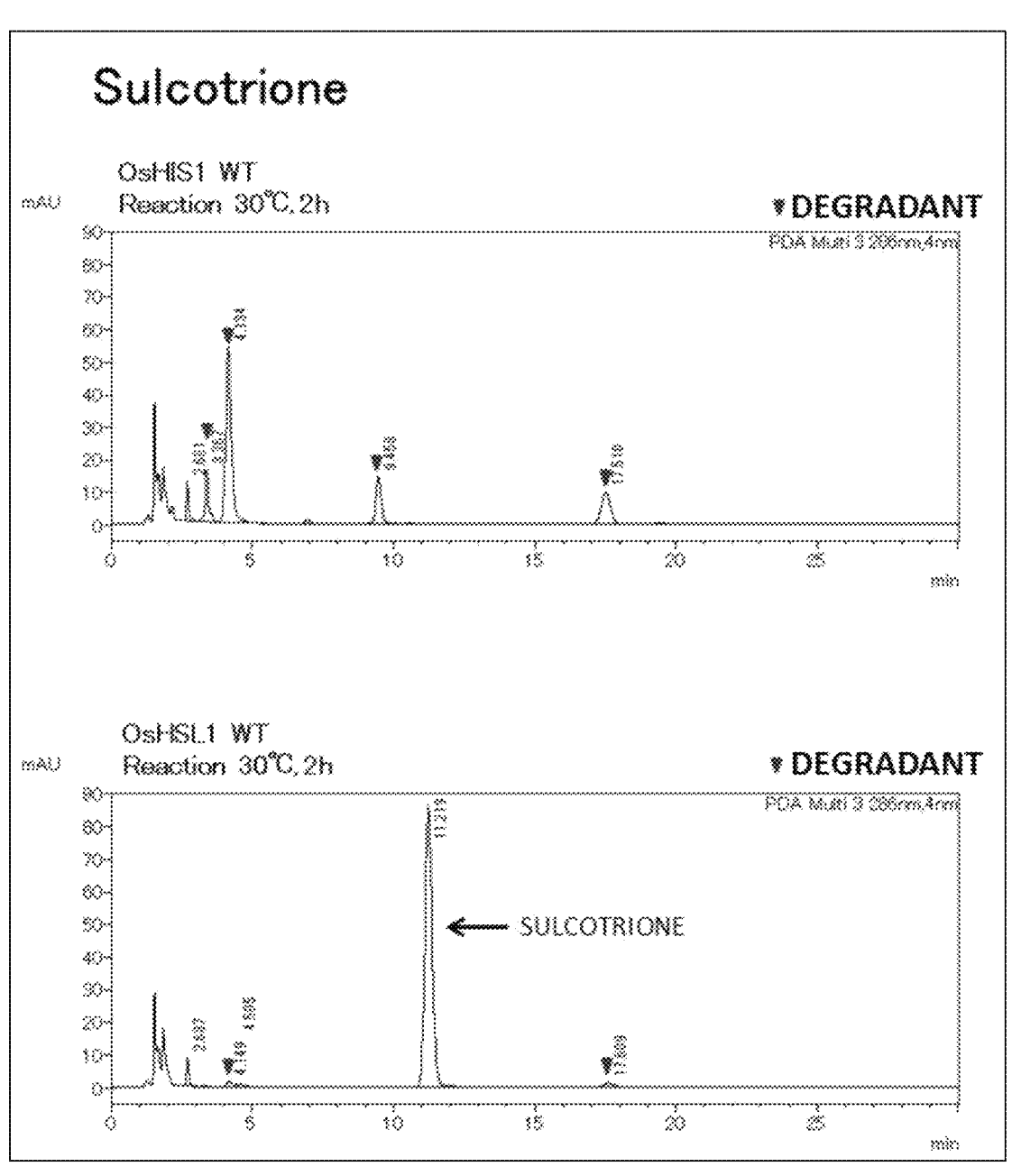
FIG. 4 is spectra showing results of analyzing sulcotrione decomposition activities of the HIS1 protein and the OsHSL1 protein using high-performance liquid chromatography, where triangles each indicate a peak derived from a degradant of sulcotrione.

As a result, as shown in FIGS. 2 to 4, it was confirmed that the HIS1 protein had a high decomposition activity to all of the 4-HPPD inhibitors, benzobicyclon hydrolysate (BBC-OH), tefuryltrione, and sulcotrione.

Note that benzobicyclon (BBC) is in the form of what is termed as a prodrug and is understood to suppress water solubility in soil and undergo hydroxylation around the root system of a plant and be absorbed mainly in the form of hydrolysate (BBC-OH) to exert its drug efficacy. Hence, since BBC-OH serves as an actual active ingredient in a plant, BBC-OH was used as an evaluation target for the present Example.

In addition, although not shown, as a result of examining the modification reaction of BBC-OH using the HIS1 protein, the reaction product was stably obtained. As a result, the modification of BBC-OH was confirmed only in the presence of divalent iron ions and 2-oxoglutarate. Moreover, as a result of analyzing the modification products of BBC-OH, tefuryltrione, and sulcotrione with the HIS1 protein by means of mass analysis, it was confirmed that all of the 4-HPPD inhibitors were each converted into a product with one oxygen atom added.

On the other hand, although the OsHSL1 protein has a high homology with the HIS1 protein at the amino acid sequence level, the decomposition activity to BBC-OH and sulcotrione was hardly observed as shown in FIGS. 2 and 3. Note that as shown in FIG. 4, it was revealed that the OsHSL1 protein hada decomposition activity to tefuryltrione, which was lower than that of the HIS1 protein, though.

Example 2

Estimation of Amino Acid Residue Involved in 4-HPPD Inhibitor Decomposition Activity in HIS1 Protein In view of this, based on this new finding, the present inventors surmised that a slight difference in amino acid sequence between the HIS1 protein and the OsHSL1 protein contributed to the decomposition activity of the 4-HPPD inhibitor. Then, the amino acid residue involved in the 4-HPPD inhibitor decomposition activity in the HIS1 protein was estimated by a method described below.

First, for the purpose of predicting the three-dimensional structure of the HIS1 protein, the present inventors attempted crystal structure analysis. However, the present inventors gave up because the purified protein was very unstable and easily insolubilized.

Instead, among oxidases dependent on divalent iron ions and 2-oxoglutarate, whose protein crystal structures have been revealed, anthocyanidin synthase, which is an enzyme of *Arabidopsis thaliana* and has the highest sequence similarity to HIS1, was used as a template to prepare the structure model of HIS1. The method was as described below.

First, the amino acid sequence of anthocyanidin synthase of *Arabidopsis thaliana* and the amino acid sequences of the rice HIS1 protein and the OsHSL1 protein were analyzed using software ClustalW (Thompson et al. CLUSTAL W: improving the sensitivity of progressive multiple sequence alignment through sequence weighting, position-specific gap penalties and weight matrix choice. Nucleic Acids Research vol. 22 pp. 4673-4680, 1994) to prepare an alignment. The homology in amino acid sequence with anthocyanidin synthase of *Arabidopsis thaliana* was 28.5% with HIS1 and 28.8% with OsHSL1. Subsequently, accession Number 1GP6 registered as the structure of the anthocyanidin synthase protein of *Arabidopsis thaliana* was selected from Protein Data Bank (rcsb.org/pdb/home/home.do), which is a public data bank of protein structures, based on information of the paper (Wilmouth et al. Structure and mechanism of anthocyanidin synthase from *Arabidopsis thaliana*. Structure vol. 10 pp. 93-103, 2002), which reported the protein three-dimensional crystal structure of anthocyanidin synthase of *Arabidopsis thaliana*. By using this 1GP6 as a template, the three-dimensional structure models of HIS1 and OsHSL1 were prepared utilizing software SWISS-MODEL (Biasini et al. SWISS-MODEL: modelling protein tertiary and quaternary structure using evolutionary information. Nucleic Acids Research vol. 42 (W1) pp. W252-W258, 2014.).

As a result, it was confirmed that an amino acid residue in which divalent iron ions are coordinated was stored in three types of proteins in common, and it was confirmed that once this residue was substituted with another amino acid, the enzyme activity of HIS1 disappeared.

Figure 5:
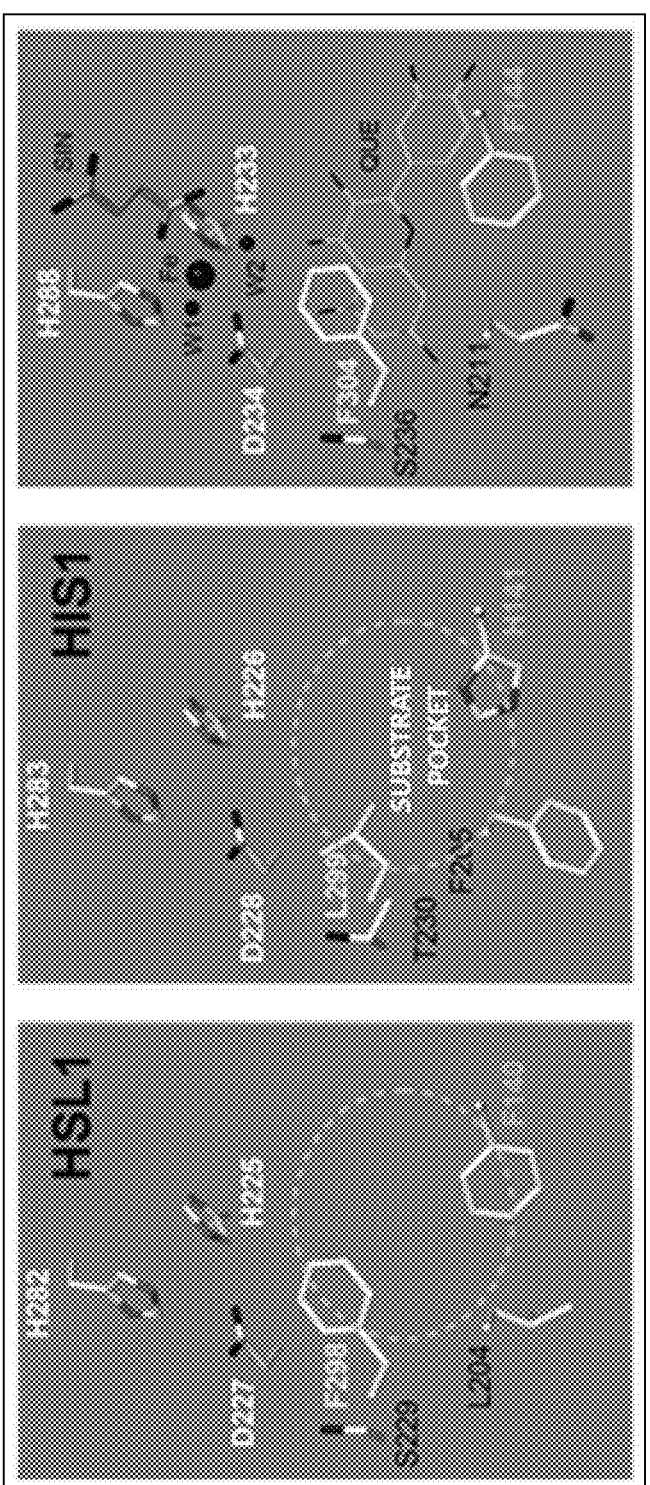
FIG. 5 is three-dimensional structure model diagrams showing amino acid residues predicted as substrate binding sites and amino acid residues predicted as surrounding substrate pockets in the HIS1 protein and the OsHSL1 protein, which are prepared using, as a template, anthocyanidin synthase of *Arabidopsis thaliana*, whose protein three-dimensional crystal structure has been interpreted (see a panel on the right side of FIG. 5).

Moreover, based on three-dimensional structure model (see FIG. 5) prepared using SWISS-MODEL regarding amino acid residues predicted as substrate binding sites and amino acid residues predicted as surrounding substrate pockets in the paper (Wilmouth et al. Structure and mechanism of anthocyanidin synthase from *Arabidopsis thaliana*. Structure vol. 10 pp. 93-103, 2002), which reported the three-dimensional crystal structure of anthocyanidin synthase protein, the present inventors compared mainly the secondary structures, that is, the α helix and β sheet structures to select amino acid residues that were different between HIS1 and OsHSL1.

Specifically, the present inventors found a possibility that among amino acid residues of the HIS1 protein which were predicted to be exposed to the substrate pocket, isoleucine at position 119 was substituted with valine at position 118 in OsHSL1, histidine at position 141 was substituted with phenylalanine at position 140 in OsHSL1, phenylalanine at position 205 was substituted with leucine at position 204 in OsHSL1, threonine at position 229 was substituted with serine at position 230 in OsHSL1, and leucine at position 299 was substituted with phenylalanine at position 298 in OsHSL1.

Example 3

Preparation of Mutants of OsHSL1 Proteins and Evaluation on 4-HPPD Inhibitor Decomposition Activities of These Mutants In view of this, to examine such possibility, amino acid residues in the OsHSL1 protein that are different from those of the HIS1 protein were substituted with those of HIS1 as appropriate and whether the enzyme activity of the HIS1 type was able to be added to the protein was analyzed by a method described below.

Design of Mutagenesis Primers

First, in order to substitute one of amino acid residues at positions 118, 140, 204, 229, and 298 of the OsHSL1 protein with that of the HIS1 protein in accordance with a site-directed mutagenesis method, mutagenesis primers used for this method were designed as illustrated below.

1) Amino-Acid Substitution of Valine Residue at Position 118 of OsHSL1 with Isoleucine Residue (HSL1 V118I)

Mutagenesis primers were designed so as to amino-acid substitute a valine residue at position 118 of OsHSL1 with an isoleucine residue. The base sequences of the mutagenesis primers are as described below. Note that lower-case letters indicate a mutated codon or an anticodon thereof.

```
V118IFW:
                                         (SEQ ID NO: 24)
5'-CGACGGCAAGAACTTCCAGattgAAGGGTATGGAACTGAC-3'

V118IRV:
                                         (SEQ ID NO: 25)
5'-GTCAGTTCCATACCCTTCaatCTGGAAGTTCTTGCCGTCG-3'
```

The att from position 20 to position 22 of the primer V118IFW (a codon corresponding to isoleucine, I) and the aat from position 19 to position 21 of the primer V118IRV (the complementary sequence of the codon att corresponding to isoleucine, I) were designed from GTG (valine, V) of a wild type OsHSL1. The valine residue at position 118 is substituted with an isoleucine residue by changing codon GTG to ATT.

2) Amino-Acid Substitution of Phenylalanine Residue at Position 140 of OsHSL1 to Histidine Residue (HSL1 F140H)

Mutagenesis primers were designed so as to amino-acid substitute a phenylalanine residue at position 140 of OsHSL1 to a histidine residue. The base sequences of the mutagenesis primers are as described below. Note that lower-case letters indicate a mutated codon or an anticodon thereof.

```
F140toH141FW:
                                         (SEQ ID NO: 26)
5'-GGTCTGATCGGCTGcatCTCAGAGTTGAACCC-3'
```

-continued
```
F140toH141RV:
                                         (SEQ ID NO: 27)
5'-GGGTTCAACTCTGAGatgCAGCCGATCAGACC-3'
```

The cat from position 15 to position 17 of the primer F140 to H141FW (a codon corresponding to histidine, H) and the atg from position 16 to position 18 of the primer F140 to H141RV (the complementary sequence of the codon cat corresponding to histidine, H) were designed from TTT (phenylalanine, F) of a wild type OsHSL1. The phenylalanine residue at position 140 is substituted with a histidine residue by changing codon TTT to CAT.

3) Amino-Acid Substitution of Leucine Residue at Position 204 of OsHSL1 with Phenylalanine Residue (HSL1 L204F)

Mutagenesis primers were designed so as to amino-acid substitute a leucine residue at position 204 of OsHSL1 with a phenylalanine residue. The base sequences of the mutagenesis primers are as described below. Note that lower-case letters indicate a mutated codon or an anticodon thereof.

```
L204toF205FW:
                                         (SEQ ID NO: 28)
5'-CAACAAAGCTCCTGCAtttgCAAGATTCAACTACTACCC-3'

L204toF205RV:
                                         (SEQ ID NO: 29)
5'-GGGTAGTAGTTGAATCTTGCaaaTGCAGGAGCTTTGTTG-3'
```

The ttt from position 17 to position 19 of the primer L204 to F205FW (a codon corresponding to phenylalanine, F) and the aaa from position 21 to position 22 of the primer F140 to H141RV (the complementary sequence of the codon ttt corresponding to phenylalanine, F) were designed from CTT (leucine, L) of the wild type OsHSL1. The leucine residue at position 204 is substituted with a phenylalanine residue by changing codon CTT to TTT.

4) Amino-Acid Substitution of Serine Residue at Position 229 of OsHSL1 with Threonine Residue (HSL1 S204T)

Mutagenesis primers were designed so as to amino-acid substitute a serine residue at position 229 of OsHSL1 with a threonine residue. The base sequences of the mutagenesis primers are as described below. Note that lower-case letters indicate a mutated codon or an anticodon thereof.

```
S229TFW:
                                         (SEQ ID NO: 30)
5'-CCTCACTCCGACGGCaccCTCTTTACGATTCTTC-3'

S229TRV
                                         (SEQ ID NO: 31)
5'-GAAGAATCGTAAAGAGggtGCCGTCGGAGTGAGG-3'
```

The acc from position 16 to position 18 of the primer S229TFW (a codon corresponding to threonine, T) and the ggt from position 17 to position 19 of the primer S229TRV (the complementary sequence of the codon acc corresponding to threonine, T) were designed from TCC (serine, S) of the wild type OsHSL1. The serine residue at position 229 is substituted with a threonine residue by changing codon TCC to ACC.

5) Amino-Acid Substitution of Phenylalanine Residue at Position 298 of OsHSL1 with Leucine Residue (HSL1 F298L)

Mutagenesis primers were designed so as to amino-acid substitute a phenylalanine residue at position 298 of OsHSL1 with a leucine residue. The base sequences of the mutagenesis primers are as described below. Note that lower-case letters indicate a mutated codon or an anticodon thereof.

```
F298toL299FW:
                                            (SEQ ID NO: 32)
5'-GGATCTCACTGGCCATGttaTACAGTGTGAATGATGAG-3'

F298toL299RV:
                                            (SEQ ID NO: 33)
5'-CTCATCATTCACACTGTAtaaCATGGCCAGTGAGATCC-3'
```

The tta from position 18 to position 20 of the primer F298 to L299FW (a codon corresponding to leucine, L) and taa from position 19 to position 21 of the primer F298 to L299RV (the complementary sequence of the codon tta corresponding to leucine, L) were designed from TTT (phenylalanine, F) of the wild type OsHSL1. The phenylalanine residue at position 298 is substituted with a leucine residue by changing codon TTT to TTA.

Preparation of Mutation-Introduced DNA

Next, site-directed mutation is introduced into OsHSL1 proteins using QuikChange II Site-Directed Mutagenesis Kit (manufactured by Agilent) and primers designed by introduction of mutation as described above.

Specifically, a plasmid AK241948/pFLC1 in which cDNA coding for the OsHSL1 protein has been cloned (provided from Gene Bank of The National Institute of Agrobiological Sciences) was used as a template and inverse PCR was conducted using the above-described mutagenesis primer set to obtain a PCR product in which mutation was introduced in the cDNA.

To be specific, the composition of the PCR reaction was obtained by mixing 5 μl of buffer provided to the kit, 1 μl of dNTP mix provided to the kit, 1 μl (2.5 units) of pfu DNA polymerase provided to the kit, 1 μl (125 ng) of each of Fw and Rv primers, 1 μl (10 ng) of template plasmid DNA, and 40 μl of distilled water. Then, 50 μl of this reaction liquid was held at 95° C. for 30 seconds, and then reaction at 95° C. for 30 seconds, at 55° C. for one minute, and at 68° C. for 4.5 minutes was repeated for 16 cycles, followed by cooling down to 4° C. to prepare the PCR product, using a PCR reaction device (TaKaRa PCR Thermal Cycler TP350 manufactured by Takara Shuzo Co., Ltd.).

Subsequently, 1 μl (10 units) of DpnI provided to the kit was added to the amplified PCR product, followed by holding at 37° C. for 1 hour. With this reaction, the template plasmid in which mutation was not introduced was cut off.

After the completion of the reaction, 1 μl of the DpnI-treated PCR product was subjected to transformation of an *Escherichia coli* competent cell provided to the kit, and a mutation-introduced plasmid was prepared from the emerged drug-resistant colony.

Then, the mutation introduced OsHSL1 protein thus prepared was prepared by a cell-free protein synthesis method using a wheat germ extract (Kanno et al. Structure-Based in Vitro Engineering of the Anthranilate Synthase, a Metabolic Key Enzyme in the Plant Tryptophan Pathway. Plant Physiology vol. 138 pp. 2260-2268, 2005).

Note that after the reaction, the reaction liquid was subjected to SDS-polyacrylamide gel electrophoresis (SDS-PAGE). The electrophoresis was then followed by CBB staining to confirm that a protein having a desired molecular weight was synthesized.

Multi Site-Directed Mutagenesis

In addition, a plurality of amino acid residues at any of positions 118, 140, 204, 229, and 298 of the OsHSL1 protein were substituted with those of the HIS1 protein by the above same method, as shown below.

6) Amino-Acid Substitution of Phenylalanine Residue at Position 140 and Leucine Residue at Position 204 of OsHSL1 with Histidine Residue and Phenylalanine Residue, Respectively (HSL1 F140H L204F)

A plasmid pFLC1-HSL1 (L204F) obtained by amino-acid substituting a leucine residue at position 204 of OsHSL1 with a phenylalanine residue was used as a template, and mutagenesis was conducted such that a phenylalanine residue at position 140 was amino-acid substituted with a histidine residue using the above-described primers F140 to H141FW and F140 to H141RV.

7) Amino-Acid Substitution of Phenylalanine Residue at Position 140 and Phenylalanine Residue at Position 298 of OsHSL1 with Histidine Residue and Leucine Residue, Respectively (HSL1 F140H F298L)

A plasmid pFLC1-HSL1 (F298L) obtained by amino-acid substituting a phenylalanine residue at position 298 of OsHSL1 with a leucine residue was used as a template, and mutagenesis was conducted such that a phenylalanine residue at position 140 was amino-acid substituted with a histidine residue using the above-described primers F140 to H141FW and F140 to H141RV.

8) Amino-Acid Substitution of Leucine Residue at Position 204 and Phenylalanine Residue at Position 298 of OsHSL1 with Phenylalanine Residue and Leucine Residue, Respectively (HSL1 L204F F298L)

A plasmid pFLC1-HSL1 (F298L) obtained by amino-acid substituting a phenylalanine residue at position 298 with a leucine residue was used as a template, and mutagenesis was conducted such that a leucine residue at position 204 was amino-acid substituted with a phenylalanine residue using the above-described primers L204 to F205FW and L204 to F205RV.

9) Amino-Acid Substitution of Phenylalanine Residue at Position 140, Leucine Residue at 204, and Phenylalanine Residue at Position 298 of OsHSL1 with Histidine Residue, Phenylalanine Residue, and Leucine Residue, Respectively (HSL1 F140H L204F F298L)

A plasmid pFLC1-HSL1 (L204F F298L) obtained by amino-acid substituting a leucine residue at position 204 and a phenylalanine residue at position 298 of OsHSL1 with phenylalanine residue and leucine residue, respectively was used as a template, and mutagenesis was conducted such that a phenylalanine residue at position 140 was amino-acid substituted with a histidine residue using the above-described primers F140 to H141FW and F140 to H141RV.

10) Amino-Acid Substitution of Phenylalanine Residue at Position 140, Leucine Residue at Position 204, Serine Residue at Position 229, and Phenylalanine Residue at Position 298 of OsHSL1 with Histidine Residue, Phenylalanine Residue, Threonine Residue, and Leucine Residue, Respectively (HSL1 F140H L204F S229T F298L)

A plasmid pFLC1-HSL1 (F140H L204F F298L) obtained by amino-acid substituting a phenylalanine residue at position 140, a leucine residue at position 204, and a phenylalanine residue at position 298 of OsHSL1 with a histidine residue, a phenylalanine residue, and a leucine residue, respectively was used as a template, and mutagenesis was conducted such that a serine residue at position 229 was amino-acid substituted with a threonine residue using the above-described primers S229TFW and S229TRV.

11) Amino-Acid Substitution of Valine Residue at Position 118, Phenylalanine Residue at Position 140, Leucine Residue at Position 204, Serine Residue at Position 229, and Phenylalanine Residue at Position 298 with Isoleucine Residue, Histidine Residue, Phenylalanine Residue, Threonine Residue, and Leucine Residue, Respectively (HSL1 V118I F140H L204F S229T F298L)

A plasmid pFLC1-HSL1 (F140H L204F S229T F298L) obtained by amino-acid substituting a phenylalanine residue at position 140, a leucine residue at position 204, a serine residue at position 229, and a phenylalanine residue at position 298 with a histidine residue, a phenylalanine residue, a threonine residue, and a leucine residue, respectively was used as a template, and mutagenesis was conducted such that a valine residue at position 118 was amino-acid substituted with an isoleucine residue using the above-described primers V118IFW and V118IRV.

Example 4

Preparation of Mutants of HSL1 Proteins (Except for OsHSL1 Protein) and Evaluation on 4-HPPD Inhibitor Decomposition Activity of These Mutants In addition, in order to evaluate the 4-HPPD inhibitor decomposition activity of a rice-derived HSL protein group except for OsHSL1 and an HSL protein group that exhibits a homology with HIS1, regarding cultivars other than rice, these proteins were prepared in accordance with a method described below.
Preparation of Cell-free Expression Constructs of HSL Proteins The preparation of artificially synthesized DNAs was requested to Eurofins Genomics, where in the artificially synthesized DNAs, the SpeI recognition sequence and the SalI recognition sequence were added to upstream and downstream of translated regions of HIS1 homologous genes (HSL genes) derived from rice (*Oryza sativa*), wheat (*Triticum aestivum*), barley (*Hordeum vulgare*), sorghum (*Sorghum biocolor*), and corn (*Zea mays*) except for HIS1 and OsHSL1 (regarding the rice-derived OsHSL2 gene, the nucleotide sequence of SEQ ID NO: 5; regarding the barley-derived HvHSL1 gene, the nucleotide sequence of SEQ ID NO: 7; regarding the barley-derived HvHSL2 gene, the nucleotide sequence of SEQ ID NO: 9; regarding the barley-derived HvHSL3 gene, the nucleotide sequence of SEQ ID NO: 11; regarding the wheat-derived TaHSL1 gene, the nucleotide sequence of SEQ ID NO: 13; regarding the wheat-derived TaHSL2 gene, the nucleotide sequence of SEQ ID NO: 15; regarding the corn-derived ZmHSL1, the nucleotide sequence of SEQ ID NO: 17; regarding the corn-derived ZmHSL2, the nucleotide sequence of SEQ ID NO: 19; regarding the sorghum-derived SbHSL1, the nucleotide sequence of SEQ ID NO: 21). The artificially synthesized DNAs obtained were processed with the restriction enzymes SpeI and SalI to isolate target genes. The genes obtained were introduced into plasmid vectors pYT08 for cell-free translation that were also processed with the same restriction enzyme, so that cell-free expression constructs pYT08-OsHSL2, TaHSL1, TaHSL2, HvHSL1, HvHSL2, HvHSL3, SbHSL1, ZmHSL1, and ZmHSL2 were prepared.
Introduction of Mutation Into ZmHSL2 and SbHSL1

Moreover, regarding rice-derived OsHSL2, the corn-derived ZmHSL2, and the sorghum-derived SbHSL1, mutation-introduced proteins into which an HIS1-type amino acid residue was introduced were prepared and their 4-HPPD inhibitor-modifying activities were examined.

To be specific, as described above, it was surmised from comparison between HIS1 and OsHSL1 that histidine at position 141 and leucine at position 299 of HIS1 were involved in the BBC-OH-modifying activity. In ZmHSL2 and SbHSL1, an amino acid corresponding to leucine at position 299 of HIS1 is the same as that of HIS1 and the other (corresponding to histidine at position 141 of HIS1) has a residue different from that of HIS1. In view of this, for ZmHSL2 and SbHSL1, histidine was mutated to the residue corresponding to position 141 of HIS1 and the activity thereof was examined. On the other hand, in OsHSL2, an amino acid corresponding to leucine at position 140 of HIS1 is the same as that of HIS1 and an amino acid corresponding to leucine at position 299 of HIS1 has a residue different from that of HIS1. In view of this, for OsHSL2, leucine was mutated to the residue corresponding to position 299 of HIS1 and the activity thereof was examined.

Mutagenesis Primer

1) Amino-Acid Substitution of Phenylalanine Residue at Position 301 of OsHSL2 with Leucine Residue (HSL2 F301L)

Like Example 3 described above, mutagenesis primers were designed so as to amino-acid substitute a phenylalanine residue at position 301 of OsHSL2 with a leucine residue. The base sequences of the mutagenesis primers are as described below. Note that lower-case letters indicate a mutated codon or an anticodon thereof.

```
Os2_F301L_Fw:
                           (SEQ ID NO: 34)
5'-ttgTATGCGGTCGATGGGGAGAAG-3'

Os2_F301L_Rv:
                           (SEQ ID NO: 35)
5'-CATGGCTACCGACATCCTCTCAC-3'
```

The ttg from position 1 to position 3 of the primer Os2_F301L_Fw (a codon corresponding to leucine, L) was designed from TTC (phenylalanine, F) of the wild type OsHSL2. The phenylalanine residue at position 301 is substituted with a leucine residue by changing codon TTC to TTG.

2) Amino-Acid Substitution of Glutamine Residue at Position 140 of ZmHSL2 with Histidine Residue (ZmHSL2 Q140H)

Like Example 3 described above, mutagenesis primers were designed so as to amino-acid substitute a glutamine residue at position 140 of ZmHSL2 with a histidine residue.

The base sequences of the mutagenesis primers are as described below. Note that lower-case letters indicate a mutated codon.

```
Zm2_Q140H_Fw:
                           (SEQ ID NO: 36)
5'-catCTAAAGGTCGAGCCAGAGG-3'

Zm2_Q140H_Rv:
                           (SEQ ID NO: 37)
5'-CAACCTGTCATTCCAGTCCAAGATG-3'
```

3) Amino-Acid Substitution of Glutamine Residue at Position 140 of SbHSL1 with Histidine Residue (SbHSL1 Q140H)

Like Example 3 described above, mutagenesis primers were designed so as to amino-acid substitute a glutamine residue at position 140 of SbHSL1 with a histidine residue. The base sequences of the mutagenesis primers are as described below. Note that lower-case letters indicate a mutated codon.

```
Sb1_Q140H_Fw:
                                    (SEQ ID NO: 38)
5'-catCTGAAGGTTGAGCCGGAGG-3'

Sb1_Q140H_Rv:
                                    (SEQ ID NO: 39)
5'-GAGTCTGTCGCTCCAGTCGAGAATG-3'
```

4) Amino-Acid Substitution of Tyrosine Residue at Position 205 of ZmHSL2 with Phenylalanine Residue (ZmHSL2 Y205F)

Like Example 3 described above, mutagenesis primers were designed so as to amino-acid substitute a tyrosine residue at position 205 of ZmHSL2 with a phenylalanine residue. The base sequences of the mutagenesis primers are as described below. Note that lower-case letters indicate a mutated codon.

```
Zm2_Y205F_Fw:
                                    (SEQ ID NO: 40)
5'-tttqCCCGCTTCAACTACTAC-3'

Zm2_Y205F_Rv:
                                    (SEQ ID NO: 41)
5'-GGCTTGGGGACTTGCTC-3'
```

Preparation of Mutation-Introduced DNA

Site-directed mutation was introduced through inverse PCR using primers designed with metagenesis. The pYT08-ZmHSL2 vector prepared as described above was used as a template and inverse PCR was conducted using the above-described mutagenesis primer set to obtain a PCR product in which mutation was introduced.

The composition of the PCR reaction contained 1×PCR buffer for KOD plus neo (manufactured by Toyobo Co., Ltd.), 0.2 mM of dNTPs, 1.5 mM of MgSO4, 0.02 units/µl of KOD plus neo (manufactured by Toyobo Co., Ltd.), 0.3 µM of the Fw and Rv primers, and 1 ng of the template DNA, which were held at 94° C. for 2 minutes, and then reaction at 98° C. for 10 seconds and at 68° C. for 2 minutes and 15 seconds was repeated for 5 cycles, followed by cooling down to 4° C. to prepare the PCR product, using a PCR reaction device (TaKaRa PCR Thermal Cycler TP350 manufactured by Takara Shuzo Co., Ltd.).

Then, 1 µl of DpnI (20 units/µl) (manufactured by Bio rab Laboratories, Inc.) was added to 20 µl of the amplified PCR product, followed by holding at 37° C. for 1 hour. With this reaction, the template plasmid in which mutation was not introduced was cut off.

After the completion of the reaction, 1 µl of the DpnI-treated PCR product was mixed with 0.5 µl of T4 polynucle-otide kinase (10 units/µl), 2.5 µl of Ligation high (manufac-tured by Toyobo Co., Ltd.), and 3.5 µl of MilliQ, followed by holding at 16° C. for 1 hour. The PCR product in which mutation was introduced through the above reactions was self-ligated and circularized to construct a mutation-intro-duced plasmid.

Protein Synthesis Through Wheat Germ Cell-Free System

First, synthesis of DNAs for transfer template was con-ducted through PCR in accordance with the following procedures. The plasmids prepared were used to prepare for templates of in vitro transfer reaction through PCR using the pYT08_Fw2 primer: 5'-CGCATCAGGCAGGAAATATT-TAGGTGAC-3' (SEQ ID NO: 42) and the pYT08_Rv primer: 5'-GGAGAAAGGCGGACAGGTATCCGGTAAG-3' (SEQ ID NO: 43). The composition of the PCR reaction contained 1×ExTaq buffer, 2 mM of dNTPs, 0.025 units/µl of KOD plus neo (manufactured by Toyobo Co., Ltd.), 0.2

µM of Fw and Rv primers, and 1 ng of template DNA, which were held at 94° C. for 2 minutes, and then reaction at 98° C. for 10 seconds and at 68° C. for 2 minutes and 15 seconds was repeated for 5 cycles, followed by cooling down to 4° C., using a PCR reaction device (TaKaRa PCR Thermal Cycler TP350 manufactured by Takara Shuzo Co., Ltd.).

Next, with the obtained PCR product as a template, transfer reaction was conducted to synthesize mRNA. The mRNA was synthesized (transferred) using the obtained PCR product directly as a template. Specifically, the PCR product was added in an amount of ¹⁄₁₀ to a transfer reaction liquid [80 mM of HEPES-KOH (pH 7.8), 16 mM of Mg (OAc)₂, 10 mM of spermidine, 10 mM of DTT, 3 mM of NTP, 1 unit/µl of RNasin RNase inhibitor (manufactured by Promega Corporation), 1 unit/µl of SP6 RNA polymerase (manufactured by Promega Corporation)]. After reaction at 37° C. for 2 hours, ethanol precipitation and 70% ethanol washing were conducted, followed by dissolving into an appropriate amount of sterile water. The absorbance at 260 nm was measured to calculate the amount of RNA.

Subsequently, with the obtained mRNA as a template, protein synthesis was conducted by the dialysis method using a wheat germ extract. Specifically, the above-de-scribed mRNA (about 30-35 µg) was added to a dialysis cup containing 50 µl of a wheat germ cell-free protein synthesis liquid. Then, the dialysis cup was immersed into a 24-well plate containing 650 µl of a substrate solution in each well, followed by incubation at 16° C. for 48 hours. After the reaction, 0.5 µl of the reaction liquid was mixed with 10 µl of a 1×loading buffer and thermal denaturation (95° C., 5 min) was conducted, followed by SDS-PAGE using a 12% polyacrylamide gel. The electrophoresis was then followed by CBB staining to confirm that a protein having a desired molecular weight was synthesized.

Then, the amounts of the synthesized proteins obtained in Examples 1 to 4 as described above were estimated as described below, followed by the analysis on the 4-HPPD inhibitor decomposition activities.

Estimation of Amount of Synthesized Protein Using Liquid Scintillation Counter

The amount of each synthesized protein was estimated by adding [¹⁴C]-Leucine to the synthesis reaction liquid to conduct cell-free protein synthesis and measuring the ¹⁴C count taken in the synthesized protein. Specifically, the mRNA and [¹⁴C]-Leucine Leucine (manufactured by Perki-nElmer Inc.) were added to inside and outside liquids in an amount of ¹⁄₁₀₀ in a dialysis cup containing 50 µl of a wheat germ cell-free protein synthesis liquid, and the dialysis cup was immersed into a 24-well plate containing 650 µl of a substrate solution in each well, followed by incubation at 16° C. for 48 hours. After the completion of the reaction, 5 µl of the reaction liquid was spotted on a paper filter 3MM CHR (manufactured by GE Healthcare), and TCA precipi-tation and ethanol washing were conducted, followed by immersion into Clear-Sol (manufactured by Nacalai Tesque, Inc.). Then, ¹⁴C count taken in the synthesized protein was measured by using a liquid scintillation counter and the total ¹⁴C count contained in the synthesized protein was calcu-lated (A). Moreover, the total ¹⁴C contained in the reaction liquid was spotted on a paper filter and the ¹⁴C count was measured in the same manner (B), the ratio of [¹⁴C] Leu taken in the synthesized protein (B/A) was calculated from these values (C). Then, the ratio of specific one residue taken in the amino acid sequence of the synthesized protein (C/D) was calculated by dividing the ratio of [¹⁴C]Leu by the number of Leus (D) contained in the amino acid sequence of the protein (E). Then, the amount of the synthesized protein (F×E×G) was calculated by multiplying this by the amino acid content (F) in the reaction liquid and the molecular weight (G) of the synthesized protein.

Enzyme Preparation

Cell-free protein synthesis was conducted without adding [$^{14}$C]-Leucine Leucine under the same conditions as those in the estimation of the synthesized amount to estimate the protein concentration of this translation reaction liquid from the above-described estimation. Then, 100 μl of the translation reaction liquid was subjected to buffer exchange to a basic translation buffer (30 mM HEPES-KOH (pH=7.8), 100 mM KOAc) by using the illustra MicroSpin G-25 column (manufactured by GE Healthcare). The amounts of Note that the 5-point scale of the decomposition activity in each of FIGS. 12 to 17 is based on a relative value of the degree of decrease in a substrate-derived peak area detected by HPLC where the degree of decrease in the HIS1 protein was designated by 5. Moreover, the amino acid portions shown in FIGS. 12, 16 and 17 indicate positions in the OsHSL1 protein of SEQ ID NO: 4; in FIGS. 13, 14, and 15, the portions are read as amino acids corresponding to these positions. In addition, Table 7 shows amino acids at the portions of the OsHSL1 protein, amino acids corresponding to the aforementioned amino acids in the other proteins, and positions of the corresponding amino acids of each of the other proteins.

TABLE 7

| OsHSL1 | Position 118 | Position 140 | Position 204 | Position 229 | Position 298 |
|---|---|---|---|---|---|
| (SEQ NO: 4) | VALINE | PHENYLALANINE | LEUCINE | SERINE | PHENYLALANINE |
| HIS1 | Position 119 | Position 141 | Position 205 | Position 230 | Position 299 |
| (SEQ NO: 2) | ISOLEUCINE | HISTIDINE | PHENYLALANINE | THREONINE | LEUCINE |
| OsHSL2 | Position 119 | Position 141 | Position 206 | Position 231 | Position 301 |
| (SEQ NO: 6) | ISOLEUCINE | HISTIDINE | THREONINE | CYSTEINE | PHENYLALANINE |
| ZmHSL2 | Position 118 | Position 140 | Position 205 | Position 230 | Position 299 |
| (SEQ NO: 20) | LEUCINE | GLUTAMINE | TYROSINE | PROLINE | LEUCINE |
| SbHSL1 | Position 118 | Position 140 | Position 205 | Position 230 | Position 299 |
| (SEQ NO: 22) | LEUCINE | GLUTAMINE | TYROSINE | PROLINE | LEUCINE | the solution before and after the buffer exchange were measured and the estimated protein concentration was corrected.

Enzyme Analyzing Method

An enzyme reaction liquid was prepared by mixing 250 mM of HEPES-KOH (pH 7.0) with a mixture liquid, which contained 0.25 mM of FeCl2, 1.5 mM of ascorbic acid, 1.5 mM of 2-oxoglutarate, and 0.75 mM of a substrate, and a translation reaction liquid, which contained a synthesized enzyme protein, in a proportion of 40% and 60%, respectively. After incubation at 30° C. for 3 hours, 100% methanol in the same amount as the enzyme reaction liquid was added and sufficiently mixed, followed by being left to stand for 5 minutes on ice. This was subjected to centrifuge separation (20, 400 g, 20 minutes, 4° C.) and the supernatant was passed through Cosmonice Filter W (0.45 μm) (manufactured by Nacalai Tesque, Inc.) to obtain a sample for high-performance liquid chromatography. The analysis on the substrate and the product before and after the enzyme reaction was conducted by loading a column_Pro C18 (150×4.6 mm I.D.) (manufactured by YMC Co., Ltd.) on a high-performance liquid chromatography device_ELITE LaChrom L-2000 series (manufactured by Hitachi, Ltd.). Elution was conducted at a flow speed of 1 mL/min and a column temperature of 40° C. under solvent conditions of acetonitrile:water (1% acetic acid)=55:45 or 50:50 (BBC-OH), acetonitrile:water (1% acetic acid)=45:55 (Sulcotrione), acetonitrile:water (1% acetic acid)=45:55 (Mesotrione), acetonitrile:water (1% acetic acid)=55:45 or 50:50 (tefryltrone), and acetonitrile:water (1% acetic acid)=55:45 or 50:50 (Tembotrione), respectively, and the compound was detected at an ultraviolet wavelength of 286 nm.

Figure 6:
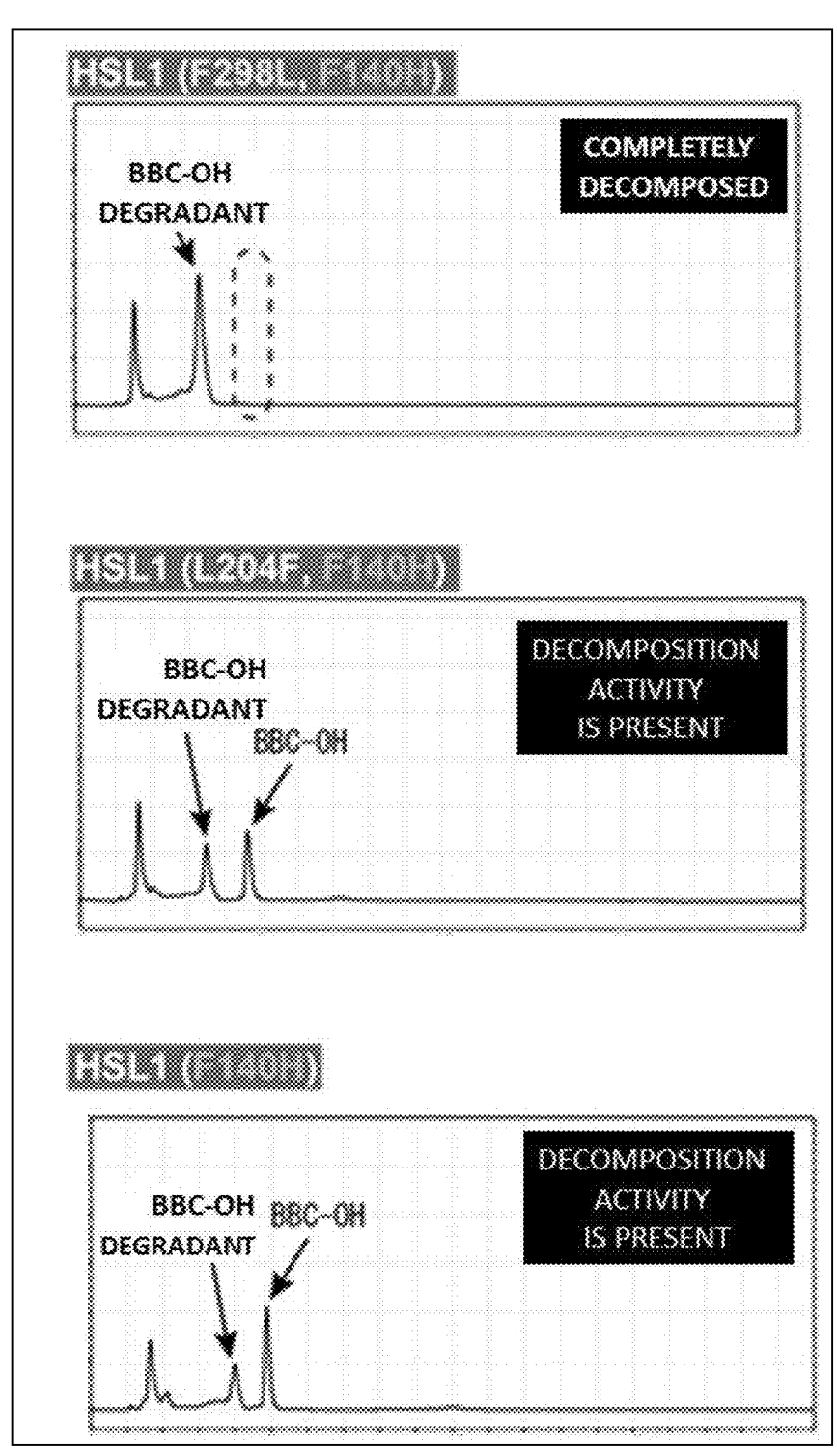
FIG. 6 is spectra showing results of analyzing BBC-OH decomposition activities of OsHSL1 protein mutants (a two-site mutant of F140H and F298L, a two-site mutant of F140H and L204F, and a single-site mutant of F140H) using high-performance liquid chromatography.
Figure 7:
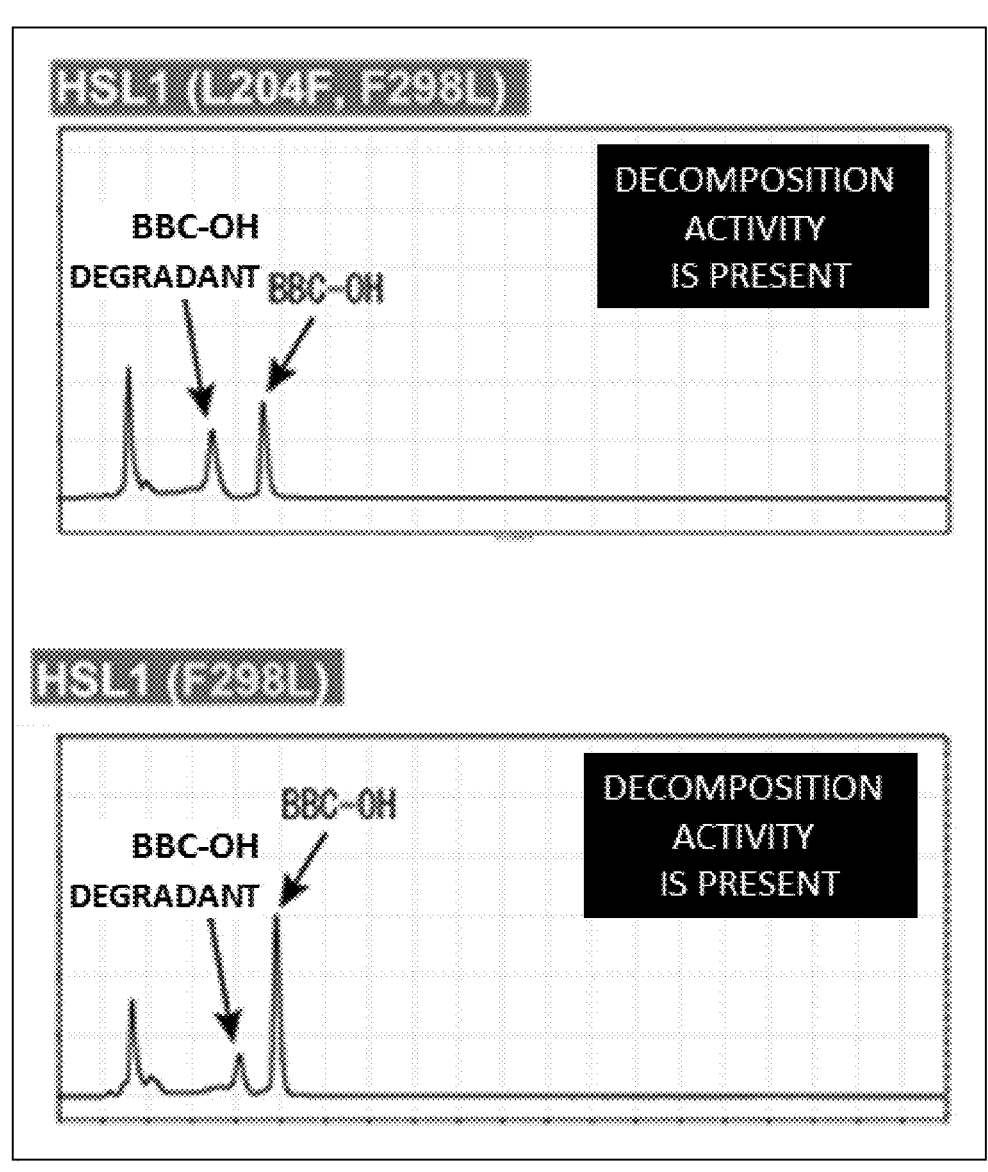
FIG. 7 is spectra showing results of analyzing BBC-OH decomposition activities of OsHSL1 protein mutants (a two-site mutant of L204F and F298L and a single-site mutant of F298L) using high-performance liquid chromatography.
Figure 8:
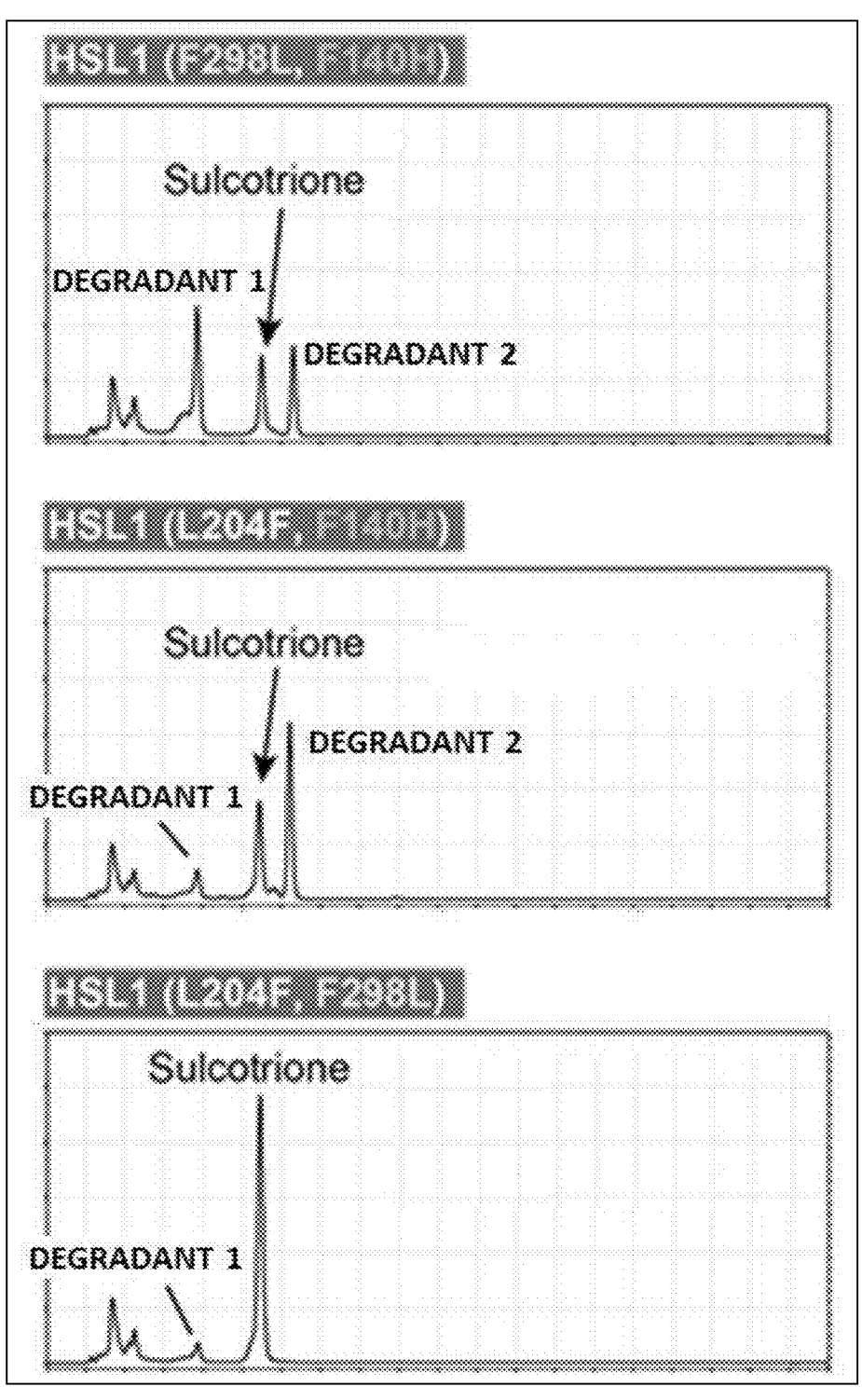
FIG. 8 is spectra showing results of analyzing sulcotrione decomposition activities of OsHSL1 protein mutants (the two-site mutant of F140H and F298L, the two-site mutant of F140H and L204F, and the two-site mutant of L204F and F298L) using high-performance liquid chromatography.
Figure 9:
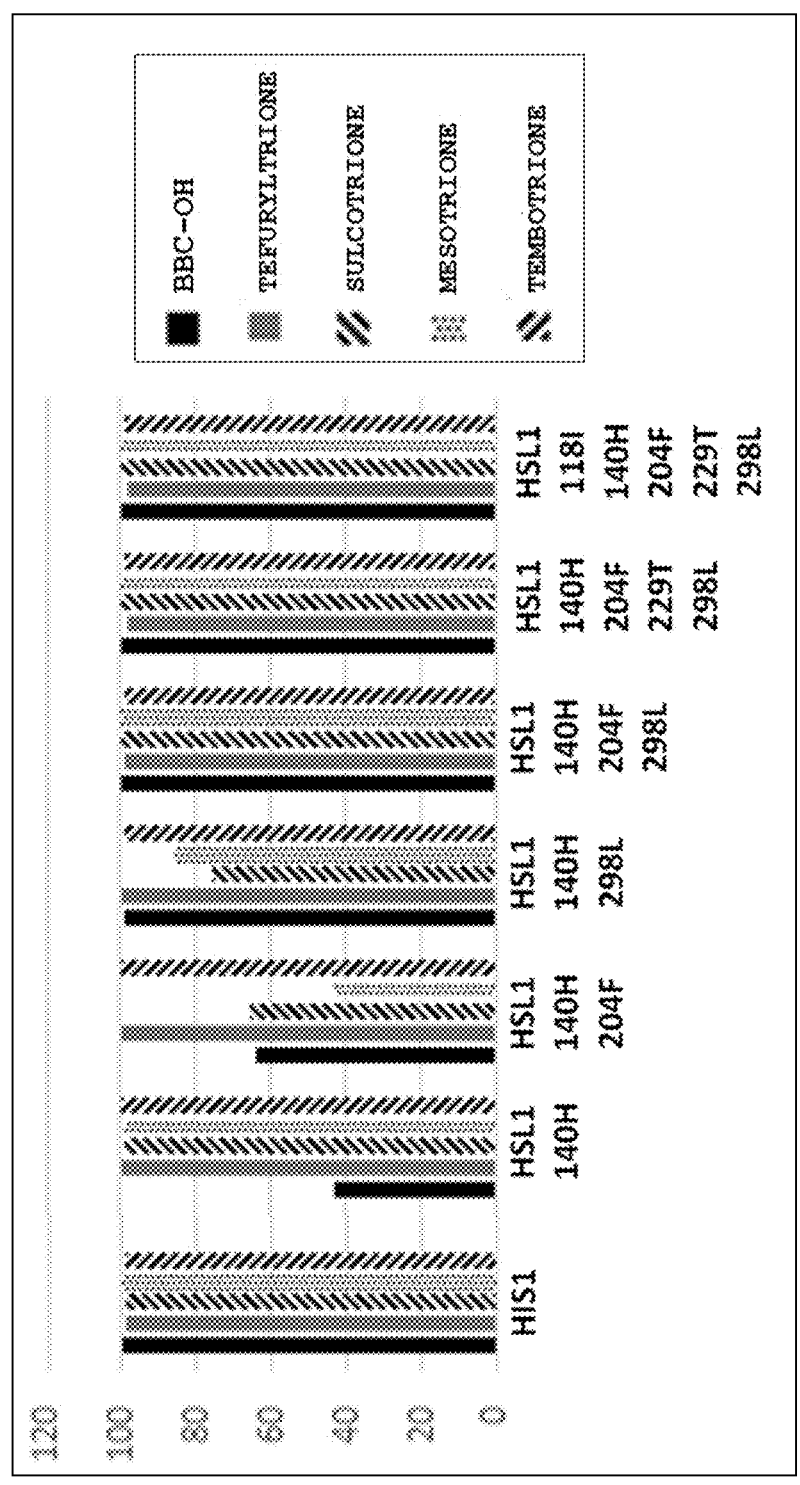
FIG. 9 is a graph showing results of analyzing decomposition activities of various mutants of the HIS1 protein and the OsHSL1 protein against various 4-HPPD inhibitors, using high-performance liquid chromatography, where "HIS1" indicates various 4-HPPD inhibitors decomposition activities of the HIS1 protein, "HSL1 140H" indicates those of the single-site mutant (F140H) of the OsHSL1 protein, "HSL1 140H 204F" indicates those of a two-site mutant (F140H and L204F) of the OsHSL1 protein, "HSL1 140H 298L" indicates those of the two-site mutant (F140H and F298L) of the OsHSL1 protein, "HSL1 140H 204F 298L" indicates those of a three-site mutant (F140H, L204F, and F298L) of the OsHSL1 protein, "HSL1 140H 204F 229T 298L" indicates those of a four-site mutant (F140H, L204F, S229T, and F298L) of the OsHSL1 protein, and "HSL1 118I 140H 204F 229T 298L" indicates those of a five-site mutant (V118I, F140H, L204F, S229T, and F298L) of the OsHSL1 protein, and where the vertical axis indicates a relative value when the values of the 4-HPPD inhibitor decomposition activities of the HIS1 protein are each set to 100.

By the above-described method, the HIS1 proteins and their homologous proteins (HSL proteins) as well as mutation-introduced products of these were evaluated in terms of the 4-HPPD inhibitor decomposition activity, and the results of the evaluation are shown in FIGS. 12 to 17. In addition, representative results are shown in FIGS. 6 to 8. Moreover, a graph in which the results of the mutation-introduced product of the HSL1 proteins were compiled is shown in FIG. 9.

Introduction of Mutation in OsHSL1 Protein

Regarding the OsHSL1 protein, in the case where the substrate was BBC-OH, only very weak decomposition activity was observed in the wild type, as shown in FIG. 12 and FIG. 2. However, as shown in FIG. 12, FIG. 6, and FIG. 9, introduction of the F140H mutation significantly increased the activities. Moreover, it was revealed that addition of the L204F mutation or addition of the F298L mutation further improved the decomposition activities of BBC-OH.

Moreover, as shown in FIG. 12, it was revealed that substitution of that portion with lysine, which is a basic amino acid like histidine, also improved the BBC-OH decomposition activity of the OsHSL1 protein, which was less effective than the introduction of the F140H mutation, though.

In addition, as shown in FIG. 12 and FIG. 7, it was revealed that introduction of the F298L mutation also improved the BBC-OH decomposition activity of the OsHSL1 protein, which was less effective than the introduction of the F140H mutation, though. Moreover, it was revealed that addition of the L204F mutation further improved the activity.

In addition, regarding the OsHSL1 protein, in the case where the substrate was tefuryltrione, as shown in FIG. 16 and FIG. 3, it was observed that even the wild type had the decomposition activity, which was less effective than that of the HIS1 protein, though. Moreover, as shown in FIG. 16, it was revealed that introduction of the F140H mutation improved the activity to as high a level as that of the HIS1 protein. On the other hand, in the introduction of the F298L mutation, it was revealed that although the tefuryltrione decomposition activity of the OsHSL1 protein decreased, addition of both mutations (F140H and F298L) allowed for as high a tefuryltrione decomposition activity as that of the HIS1 protein again.

Furthermore, as shown in FIG. 16, it was revealed that substitution of that portion with lysine, which is a basic amino acid like histidine, also improved the tefuryltrione decomposition activity of the OsHSL1 protein, which was less effective than the introduction of the F140H mutation, though.

In addition, regarding the OsHSL1 protein, in the case where the substrate was sulcotrione, only very weak decomposition activity was observed in the wild type, as shown in FIG. 17 and FIG. 4. However, as shown in FIG. 17 and FIG. 9, it was revealed that introduction of the F140H mutation improved the activity to as high a level as that of the HIS1 protein. On the other hand, as shown in FIG. 8 and FIG. 9, it was also revealed that addition of the L204F mutation or addition of the F298L mutation decreased the sulcotrione decomposition activity.

In addition, as shown in FIG. 17, it was revealed that even when the F140H mutation was not introduced, introduction of the L204F mutation and the F298L mutation improved the sulcotrione decomposition activity. Moreover, although not shown in the figures, regarding mesotrione and tembotrione as well, it was revealed that this 2-site mutagenesis improved the decomposition activity.

Moreover, as shown in FIG. 17, substitution of that portion with arginine, which is a basic amino acid like histidine, also improved the sulcotrione decomposition activity of the OsHSL1 protein, which was less effective than the introduction of the F140H mutation, though.

In addition, regarding the OsHSL1 protein, in the case where the substrate was mesotrione or tembotrione, although not shown in the figures, only very weak decomposition activity was observed in the wild type. However, it was revealed that introduction of the F140H mutation improved the activities in both cases to as high a level as that of the HIS1 protein.

Introduction of Mutation in OsHSL2 Protein

Regarding the OsHSL2 protein, in the case where the substrate was BBC-OH, only very weak decomposition activity was observed in the wild type, as shown in FIG. 13. However, it was revealed that introduction of the F298L mutation was improved the BBC-OH decomposition activity of the OsHSL2 protein.

Introduction of Mutation in ZmHSL2 Protein

Regarding the ZmHSL2 protein, in the case where the substrate was BBC-OH, as shown in FIG. 14, it was revealed that even the wild type had the decomposition activity, which was less effective than that of the HIS1 protein, though. Moreover, it was revealed that introduction of the Q140H mutation improved the activity to as high a level as that of the HIS1 protein. In addition, it was also revealed further introduction of the Y204F mutation further improved the activity.

In addition, although not shown in the figures, regarding the ZmHSL2 protein, it was also found that in the case where the substrate was sulcotrione, introduction of the Q140H mutation improved the activity.

Introduction of Mutation in SbHSL1 Protein

Regarding the SbHSL1 protein, in the case where the substrate was BBC-OH, as shown in FIG. 15, it was confirmed that even the wild type had the decomposition activity, which was less effective than that of the HIS1 protein, though. Moreover, it was revealed that introduction of the Q140H mutation improved the activity to as high a level as that of the HIS1 protein.

As described above, in the case where any of benzobicyclon hydrolysate (BBC-OH), tefuryltrione, sulcotrione, mesotrione, and tembotrione, or a 4-HPPD inhibitor of any of these was used as the substrate, it was revealed that substituting the amino acid at position 140 with a basic amino acid, particularly histidine, improved the decomposition activity of the HSL protein.

In addition, as shown in FIG. 9, it was also revealed that in the case where BBC-OH was used as the substrate, the addition of the L204 mutation or the addition of the F298 mutation further improved the decomposition activity; on the other hand, in the case where tefuryltrione, sulcotrione, or mesotrione was used as the substrate, the decomposition activity did not change or decreased.

Moreover, it was revealed that the introduction of mutation into three portions F140, L204, and F298 improved all of the decomposition activities against BBC-OH, tefuryltrione, sulcotrione, mesotrione, and tembotrione to as high a level as that of the HIS1 protein.

Example 5

Evaluation on Resistance of OsHSL1 Mutant Against 4-HPPD Inhibitor in Plant (*Arabidopsis thaliana*)

OsHSL1 mutants (a five-site mutant of V118I, F140H, L204F, S229T, and F298L, a four-site mutant of F140H, L204F, S229T, and F298L, and a three-site mutant of F140H, L204F, and F298L) to which the decomposition activity against benzobicyclon hydrolysate (BBC-OH) was added in the above-described in vitro system were expressed in plants, and whether the resistance to benzobicyclon (BBC) in the form of a prodrug were enhanced was evaluated by a method described below.

Specifically, first, genes coding for each OsHSL1 mutant was prepared in the same manner as described above. Then, each gene was linked to downstream of the 35S promoter and was cloned together with a kanamycin-resistance gene cassette in the binary vector. The vectors thus obtained were each introduced into *Arabidopsis thaliana* (Columbia) by a floral dip method and transformed. T0 seeds thus obtained were seeded in a kanamycin-containing medium and resistant individuals were obtained. Then, individuals determined to have the gene introduced therein were selected, from which T1 seeds were collected and seeded in a BBC-containing growth medium. The growth conditions of these were observed. The results thus obtained are shown in FIG. 10.

Figure 10:
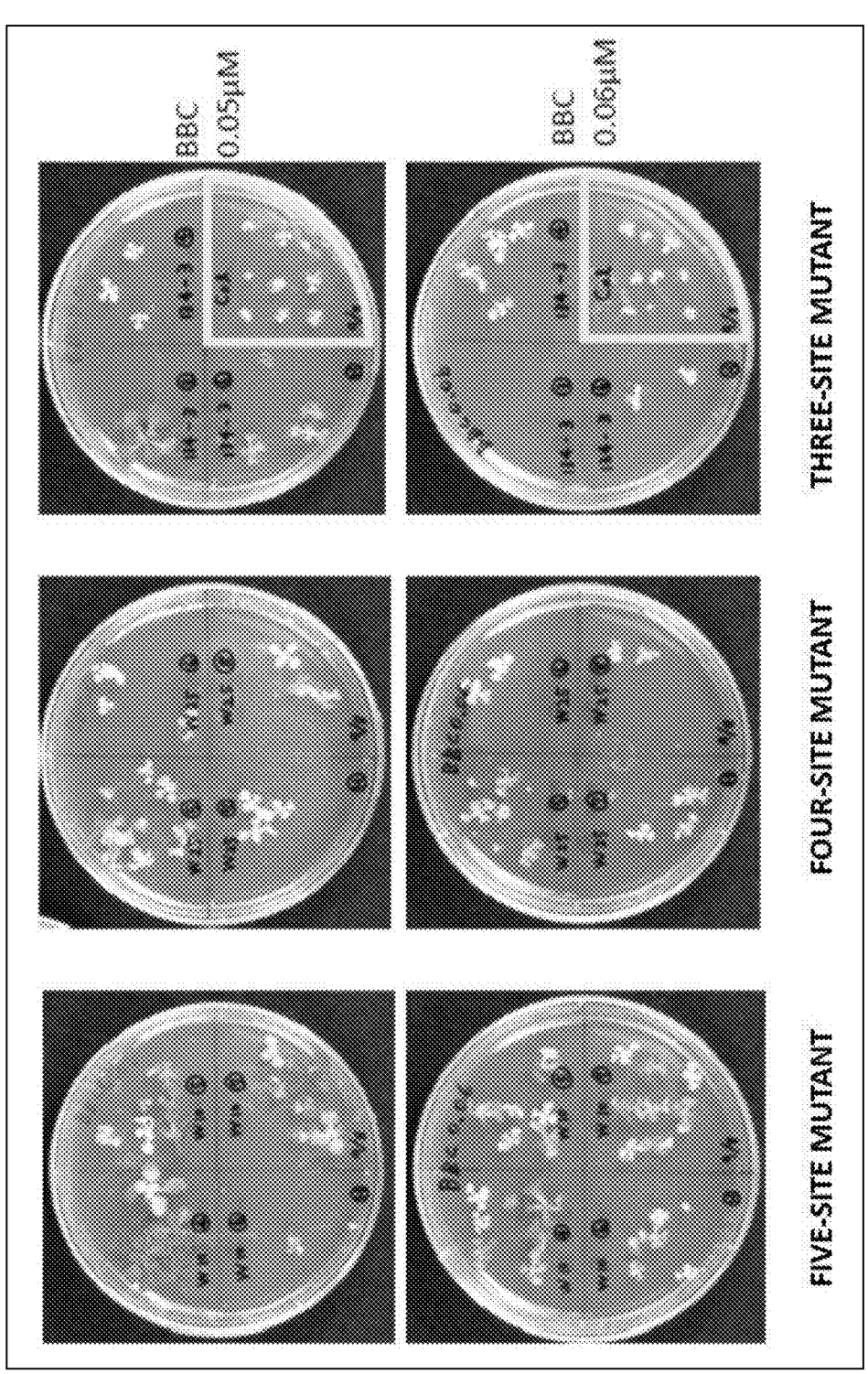

As is clear from the results shown in FIG. 10, in any of the mutants, it was observed that individuals that took in green appeared under conditions in which non-recombinant control individuals were whitened. To be more specific, apparent resistance against BBC was observed in one out of 3 lines of *Arabidopsis thaliana* in which the three-site mutant was expressed, was observed in one out of 4 lines of *Arabidopsis thaliana* in which the four-site mutant was expressed, and was observed in three out of 4 lines of *Arabidopsis thaliana* in which the five-site mutant was expressed. In other words, it was confirmed that expressing the OsHSL1 mutant provided with the 4-HPPD inhibitor decomposition activity in a plant enhanced the resistance of the plant against the 4-HPPD inhibitor.

In addition, a single-site mutant of F140H or a single-site mutant of F298L was expressed in *Arabidopsis thaliana*, and it was evaluated whether the resistance against sulcotrione (the concentration of sulcotrione contained in the growth medium: 0.1 μM), mesotrione (the concentration of mesotrione contained in the growth medium: 0.1 μM), or tembotrione (the concentration of tembotrione contained in the growth medium: 0.05 μM) was enhanced in the same manner as described above.

As a result, although not shown in the figures, in the single-site mutant of F140H, it was observed that individuals that took in green appeared under conditions in which non-recombinant control individuals (HSL1 (wild type)) were whitened, and the efficacy of the mutation in improvement of the resistance against the agent was confirmed as in the case of the above-described in vitro system. On the other hand, in the single-site mutant of F298L, no improvement of the resistance against the agent was confirmed.

Example 6

Evaluation on Resistance of OsHSL1 Mutant to 4-HPPD Inhibitor in Plant (Rice)

Next, the efficacy of the F140H mutation was confirmed using rice. Specifically, first, an mHSL1 gene obtained by modifying phenylalanine at position 140 in a rice HSL1 cDNA gene to histidine was prepared. Subsequently, the mutated gene or an HSL1 gene in which the mutation was not introduced was linked to downstream of the 35S promoter and was cloned together with a hygromycin-resistance gene expression cassette in the binary vector. Then, these vectors were each introduced into a benzobicyclon-susceptible cultivar "Yamadawara" by an *agrobacterium* method and recombinant rice was grown.

The recombinant rice (T1) seeds thus produced and the seeds of the original cultivar "Yamadawara" were tested and seeded on an MS medium containing 0.25 μM BBC in a sterile manner and grown at 30° C. in a bright place for 8 days. Results thus obtained are shown in FIG. 11.

As is clear from the results shown in FIG. 11, in the mHSL1 recombinant rice, individuals that took in green appeared under conditions in which the non-recombinant control (original cultivar) and non-modified HSL1 recombinant rice were whitened (Note that since it is a hetero-population, individuals that were whitened also appeared. However, in this experiment, null individuals generated due to gene separation were removed.

In this way, it was confirmed that in rice as well, BBC resistance was added to the BBC-susceptible cultivar by overexpressing the mHSL1 (F140H) gene.

INDUSTRIAL APPLICABILITY

As described so far, according to the present invention, it is possible to increase the catalytic activity of an HSL protein to oxidize a 4-HPPD inhibitor in a 2-oxoglutarate-dependent manner by mutating, in the protein, position 140 to a basic amino acid. Then, in the present invention, it is also possible to produce a plant with increased resistance to a 4-HPPD inhibitor by utilizing such a method for producing an HSL protein with increased catalytic activity to oxidize a 4-HPPD inhibitor in a 2-oxoglutarate-dependent manner.

Moreover, as described above, based on the finding that an amino acid at position 140 in an HSL protein is an amino acid that affects the catalytic activity, according to the present invention, it is also possible to determine resistance of a test plant to a 4-HPPD inhibitor by detecting a nucleotide which codes for an amino acid at position 140 in an HSL gene of the test plant. In addition, according to the present invention, it is also possible to provide a method for breeding a plant having increased resistance to a 4-HPPD inhibitor, utilizing the above method.

Therefore, when plants having increased resistance to a 4-HPPD inhibitor of the present invention are used and cultivated, the weed control can be efficiently carried out in cultivation paddy fields or cultivation fields. In addition, the method for determining resistance of a plant to a 4-HPPD inhibitor of the present invention can be utilized, for example, to reduce a germination risk of self-sown seeds from the previous year in crop rotation cycles. In this manner, the present invention can contribute greatly to stable production and yield increase of useful plants.

SEQUENCE LISTING FREE TEXT

SEQ ID NO: 23
<223> catalytic triad
<223> Xaa at position 2 may be any amino acid.
<223> Xaa at position 3 is aspartic acid or glutamic acid.
<223> Xaa at position 4 may be any amino acid.
SEQ ID NOs: 24 to 43
<223> sequence of artificially synthesized primers

---

The invention claimed is:

1. A method for producing a mutant HSL (4-Hydroxy-phenylpyruvate dioxygenase Inhibitor sensitive 1-Like) protein with increased catalytic activity to oxidize a 4-HPPD (4-hydroxyphenylpyruvate dioxygenase) inhibitor in a 2-oxoglutarate-dependent manner, said method comprising:

expressing, in a plant cell, a mutant HSL protein, wherein said mutant HSL protein is a mutant of a wild type HSL protein, wherein said wild type HSL protein comprises an amino acid sequence having at least 95% sequence identity to the amino acid sequence of SEQ ID NO: 6, wherein the mutant HSL protein comprises a substitution of phenylalanine to leucine at a position corresponding to position 298 of SEQ ID NO:4, and wherein said mutant HSL protein has no more than one substitution relative to the wild type HSL protein.

2. A method for producing a plant with increased resistance to a 4-HPPD inhibitor, comprising the steps of:

(I) mutating, in a plant cell, an endogenous gene encoding a wild type HSL protein, wherein said wild type HSL protein comprises an amino acid sequence having at least 95% sequence identity to the amino acid sequence of SEQ ID NO: 6, wherein said mutating produces a mutated gene that encodes a mutant HSL protein, wherein the mutant HSL protein comprises the substitution of a phenylalanine to leucine at a position corresponding to position 298 of SEQ ID NO: 4, and wherein said mutant HSL protein has no more than one substitution relative to the wild type HSL protein; and (II) regenerating a plant from the plant cell, wherein the regenerated plant comprises said mutated gene.

* * * * *